US009549897B2

(12) United States Patent
McCarty

(10) Patent No.: US 9,549,897 B2
(45) Date of Patent: Jan. 24, 2017

(54) TRANSMUCOSAL HORMONE DELIVERY SYSTEM

(71) Applicant: PHARMACEUTICAL PRODUCTIONS INC., Miami Springs, FL (US)

(72) Inventor: John A. McCarty, Miami Springs, FL (US)

(73) Assignee: PHARMACEUTICAL PRODUCTIONS, INC., Miami Springs, FL (US)

( * ) Notice: Subject to any disclaimer, the term of this patent is extended or adjusted under 35 U.S.C. 154(b) by 0 days.

(21) Appl. No.: 14/978,459

(22) Filed: Dec. 22, 2015

(65) Prior Publication Data
US 2016/0120796 A1 May 5, 2016

Related U.S. Application Data

(60) Division of application No. 14/212,068, filed on Mar. 14, 2014, now Pat. No. 9,254,294, and a continuation-in-part of application No. 10/545,774, filed as application No. PCT/US2004/005490 on Feb. 24, 2004, now Pat. No. 8,992,974, said application No. 14/212,068 is a continuation-in-part of application No. 13/633,924, filed on Oct. 3, 2012, now Pat. No. 8,992,948, which is a continuation of application No. 12/595,183, filed as application No. PCT/US2008/004615 on Apr. 10, 2008, now abandoned.

(60) Provisional application No. 61/782,001, filed on Mar. 14, 2013, provisional application No. 60/449,647, filed on Feb. 24, 2003, provisional application No. 60/922,921, filed on Apr. 11, 2007.

(51) Int. Cl.
A61K 9/00 (2006.01)
A61K 31/565 (2006.01)
A61K 31/137 (2006.01)
A61K 31/4468 (2006.01)
A61K 31/663 (2006.01)
A61K 31/216 (2006.01)

(52) U.S. Cl.
CPC ............ A61K 9/006 (2013.01); A61K 31/137 (2013.01); A61K 31/216 (2013.01); A61K 31/4468 (2013.01); A61K 31/565 (2013.01); A61K 31/663 (2013.01)

(58) Field of Classification Search
CPC .................................................... A61K 9/006
See application file for complete search history.

(56) References Cited

U.S. PATENT DOCUMENTS

| 4,816,247 | A | 3/1989 | Desai et al. |
|---|---|---|---|
| 4,908,389 | A | 3/1990 | Mahjour et al. |
| 5,073,374 | A | 12/1991 | McCarty |
| 5,112,616 | A | 5/1992 | McCarty |
| 5,132,114 | A | 7/1992 | Stanley et al. |
| 5,135,753 | A | 8/1992 | Baker et al. |
| 5,200,393 | A | 4/1993 | Weiner |
| 5,354,560 | A | 10/1994 | Lovrecich |
| 5,373,022 | A | 12/1994 | Fawzi et al. |
| 5,374,645 | A | 12/1994 | Kurihara-Bergstrom et al. |
| 5,449,521 | A | 9/1995 | Lovrecich |
| 5,549,906 | A | 8/1996 | Santus |
| 5,662,920 | A | 9/1997 | Santus |
| 5,688,520 | A | 11/1997 | Karsenty et al. |
| 5,711,961 | A | 1/1998 | Reiner et al. |
| 5,900,247 | A | 5/1999 | Rault |
| 6,242,004 | B1 | 6/2001 | Rault |
| 6,248,760 | B1 | 6/2001 | Wilhelmsen |
| 6,255,502 | B1 | 7/2001 | Penkler et al. |
| 6,264,981 | B1 | 7/2001 | Zhang et al. |
| 6,395,713 | B1 | 5/2002 | Beigelman et al. |
| 6,479,540 | B1 | 11/2002 | Constantinides et al. |
| 6,495,154 | B1 | 12/2002 | Tam et al. |
| 6,500,456 | B1 | 12/2002 | Capella |
| 6,620,836 | B1 | 9/2003 | Patrick |
| 6,630,498 | B2 | 10/2003 | Gudipati et al. |
| 8,992,948 | B2 | 3/2015 | McCarty |
| 8,992,974 | B2 | 3/2015 | McCarty |
| 2003/0235596 | A1 | 12/2003 | Gao et al. |

FOREIGN PATENT DOCUMENTS

| EP | 0387647 | 9/1990 |
|---|---|---|
| EP | 0514373 | 6/1995 |
| JP | 2001508027 | 6/2001 |
| JP | 2001517624 | 10/2001 |
| JP | 2001521882 | 11/2001 |
| WO | 9802187 | 1/1998 |

(Continued)

OTHER PUBLICATIONS

"Pharmacokinetic Investigation of a Nicotine Sublingual Tablet", Department of Clinical Pharmacology, Pharmacia & Upjohn Consumer Healthcare, Lund, Sweden, Lars.Molander@eu.pnu.com, Jan.-Feb. 2001;56(11):813-9 (Abstract).

(Continued)

Primary Examiner — Paul Zarek
(74) Attorney, Agent, or Firm — Ann-Louise Kerner; DLA Piper LLP (US)

(57) ABSTRACT

The present invention provides a pharmaceutical composition for sublingual or buccal administration of actives with low to poor aqueous solubility, e.g. the hormone estradiol, which contains a solution of the active in a pharmaceutically acceptable solvent adsorbed or absorbed onto particles of a pharmaceutically acceptable carrier and methods of preparing and using the pharmaceutical composition.

16 Claims, 8 Drawing Sheets

(56) References Cited

FOREIGN PATENT DOCUMENTS

| WO | 9915171 | 4/1999 |
|---|---|---|
| WO | 9922703 | 5/1999 |
| WO | 0122937 | 4/2001 |
| WO | 03055486 | 7/2003 |
| WO | 2004075877 | 9/2004 |
| WO | 2010144943 | 12/2010 |

OTHER PUBLICATIONS

Amidon et al. (1995) A Theoretical Basis for a Biopharmaceutic Drug Classification: The Correlation of in Vitro Drug Product Dissolution and in Vivo Bioavailability, Pharmaceutical Research, 12(3):413-420.

Amir, S. (1998) Buccal Mucosa as a Route for Systemic Drug Delivery: A Review, 1 J. Pharm. Pharmaceut. Sci. 15:18-20.

Augsburger et al. (1966) Effect of Glidants in Tableting, J. Pharm. Sci. 55(4):418-423.

Benes et al. (1997) Transmucosal, oral controlled-release, and transdermal drug administration in human subjects: a crossover study with melatonin, J. Pharm. Sci. 86(10):1115-11159.

Bullen et al. (2010) Effect of an electronic nicotine delivery device (e cigarette) on desire to smoke and withdrawal, user preferences and nicotine delivery: randomized cross-over trial, Tobacco Control 19:98-103.

Fagerstrom et al. (2008) Pharmacological treatments for tobacco dependence, Eur. Respir. Rev. 17(10):192-198.

Gallarte et al. (1993) Preparation and evaluation in vitro of solutions and o/w microemulsions containing levobunolol as ion-pair, International J. Pharma. 100:219-225.

Hatanaka et al. (2000) Ion pair skin transport of a zwitterionic drug, cephalexin, J. Controlled Release 66:63-71.

Trotta et al. (2002) Influence of ion pairing on topical delivery of retinoic acid from microemulsions, J. Controlled Release, 86:315-321.

Takeuchi et al. (2005) Solid Dispersion Particles of Amorphous Indomethacin with fine Porous Silica Particles by Using Spray Drying Method, Intl. J. Pharma. 293:155-164.

International Search Report for International Application No. PCT/US2004/005490, mailed Aug. 9, 2004 (4 pages).

Leipold et al. (1993) Nicotine permeation through buccal cultures, Proceed. Intern. Symp. Control. Rel. Bioact. Mater., 20:242-243.

Megwa et al. (2000) Effect of ion pairing with alkylamines on the in-vitro dermal penetration and local tissue disposition of salicylates, J. Pharm. Pharmacol. 52:929-940.

Neubert, R. (1989) Ion Pair Transport Across Membranes, Pharma. Res. 6(9):743-747.

Nicorette 15mg Patch or Boots NicAssist 15 mg Patch: Summary of Product Characteristics last updated on Apr. 29, 2010.

Nicorette Nasal Spray: Summary of Product Characteristics last updated Dec. 14, 2009.

Nicorette.RTM. Inhaler/Boots NicAssist 10 mg Inhalator: Summary of Product Characteristics last updated Apr. 7, 2010.

Valenta et al. (2000) The dermal delivery of lignocaine: influence of ion pairing, International J. Pharma. 197:77-85.

Ogiso et al. (1991) Enhancement Effect of Lauric Acid on the Rectal Absorption of Propranolol from Suppository in Rats, Chem. Pharm. Bull. 39(10):2657-2661.

Pomerleau et al. (1992) Controlled dosing of nicotine via an Intranasal Nicotine Aerosol Delivery Device (INADD), Psychopharmacology 108:519-526.

Quintanar-Guerro et al. (1997) Applications of the Ion-Pair Concept of Hydrophilic Substances with Special Emphasis on Peptides, Pharma. Res. 14(2):119-127.

Repka et al. (2004) Matrix- and Reservoir-Based Transmucosal Delivery Systems: Tailoring Delivery Systems, Amer. J. Drug Delivery 2(3):173-192.

Russell et al. (1987) Nicotine Replacement in Smoking Cessation: Absorption of Nicotine Vapor From Smoke-Free cigarettes, JAMA, 257(23):3262-3265 (Abstract).

Senel et al. (2001) Drug permeation enhancement via buccal route: possibilities and limitations, J. Controlled Release, 72:133-144.

Thornley et al. (2009) A single-blind, randomized, crossover trial of the effects of a nicotine pouch on the relief of tobacco withdrawal symptoms and user satisfaction, Nicotine & Tobacco Research Advance Access, pp. 1-7.

Yajaman et al. (2006) Buccal Bioadhesive Drug Delivery—A Promising Option for Orally Less Efficient Drugs, J. Control. Rel. 114(1):15-40.

COMPARATIVE ORAL MUCOSAL PERMEATION 0.5 mg Estradiol Sublingual Tablet Manufacturing

TRANSMUCOSAL HORMONE DELIVERY SYSTEM

CROSS-REFERENCE TO RELATED APPLICATIONS

This application is a divisional of U.S. Ser. No. 14/212,068, filed on Mar. 14, 2014, which claims benefit of the priority of U.S. Provisional Application Ser. No. 61/782,001, filed on Mar. 14, 2013. U.S. Ser. No. 14/212,068 is a continuation-in-part of U.S. application Ser. No. 10/545,774, filed on Aug. 8, 2006 (now U.S. Pat. No. 8,992,974), which is a 371 of PCT/US04/05490 filed on Feb. 24, 2004, which claims priority to U.S. Provisional Application Ser. No. 60/449,647 filed on Feb. 24, 2003. U.S. Ser. No. 14/212,068 is a continuation-in-part of U.S. application Ser. No. 13/633,924, filed on Oct. 3, 2012 (now U.S. Pat. No. 8,992,948), which is a continuation of Ser. No. 12/595,183, filed on Oct. 8, 2009, and now abandoned, which is a 371 of PCT/US2008/004615 filed on Apr. 10, 2008, which claims priority to U.S. Provisional Application Ser. No. 60/922,921, filed on Apr. 11, 2007. The contents of each are incorporated by reference herein in their entirety.

SUMMARY OF THE INVENTION

The present invention provides a pharmaceutical composition that contains an ionizable pharmaceutical agent and a one or more complementary lipophilic species where the ionizable pharmaceutical agent and the one or more complementary lipophilic species are formulated in a transmucosal dosage form. In certain embodiments of the invention, the ionizable pharmaceutical agent is hydrogen-bonded to the complementary lipophilic species, or is ion-paired to the complementary lipophilic species, to form a lipophilic association (LA). The pharmaceutical composition may further contain a solvent having a dielectric constant less than that of water, wherein the LA is solvated in the solvent to form a solubilized LA. Examples of solvents include ethanol, ethyl acetate, isopropyl alcohol, triacetin, triethyl citrate, tributyl citrate, a polyethylene glycol, propylene glycol, bisabolol, glycerin, mineral oil, ethyl oleate, fatty acid esters, squalane, animal oils, vegetable oils, hydrogenated vegetable oils, isopropyl myristate, isopropyl palmitate, glycofurol, terpenes, essential oils, alcohols, polyols, or silicone fluids. The pharmaceutical composition of the present invention may further contain a carrier, wherein the LA, or solubilized LA, is adsorbed or absorbed to the carrier. The carrier may be, for example a silica or a silicified microcrystalline cellulose. The pharmaceutical composition of the present invention may further contain a water-soluble excipient. Such an excipient may possess a dielectric constant less than the dielectric constant of water. Examples of water-soluble excipients useful in the present invention include sugar, polyol, alcohol, saccharide, polysaccharide, glycerin, propylene glycol, ethanol, isopropyl alcohol, ethyl acetate, triacetin, triethyl citrate, tributyl citrate, a dextrate, dextrin, dextrose, fructose, lactitol, lactose, erythritol, maltose, maltitol, maltodextrin, polydextrose, trehalose, mannitol polyethylene glycol, sorbitol, sucrose or xylitol.

In the present invention, the molar ratio of lipophilic species to ionizable pharmaceutical agent is at least about 1:1. In one embodiment, the pharmaceutical agent possesses a basic functional group and the lipophilic species is an acid. In the present invention, the lipophilic species is a fatty acid, a long-chain alkyl sulfonic acid, or a long-chain alkyl sulfuric acid. Examples of long-chain alkyls that are found in the fatty acid, sulfonic acid or sulfuric acid are caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic acid.

In an alternative, the pharmaceutical agent possesses an acidic functional group and the lipophilic species is a base. In certain embodiments, the lipophilic species is a amine or amide, such as cetrimide, oleamidopropyl dimethylamine, didecyldimethyl ammonium chloride, a quaternary surfactant, cetylpyridinium chloride, hexetidine, benzalkonium chloride or an amine or amide of caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic or clupanadonic acid.

In certain embodiments of the present invention the carrier is capable of forming an inclusion complex with the LA or solubilized LA. The pharmaceutical composition of the present invention may further contain a carrier, wherein the LA, or solubilized LA, is adsorbed or absorbed to the carrier. The carrier may be, for example a silica or a silicified microcrystalline cellulose.

Examples of pharmaceutical agents that may be used in embodiments of the present invention include one or more of the following: a antihypertensive agent, analgesic, antidepressant, opioid agonist, anesthetic, antiarrhythmic, antiarthritic, antispasmodic, ACE inhibitor, decongestant, antibiotic, antihistamine, anti-anginal, diuretic, anti-hypotensive agent, anti-Parkinson agent, bronchodilator, oxytocic agent, anti-diuretic, anti-hyperglycemic, antineoplastic and/or immunosuppresent agent, antiemetic, anti-infective, antifungal, antiviral, antimuscarinic, antidiabetic agent, antiallergy agent, anxiolytic, sedative, antipsychotic, bone modulating agent, cardiovascular agent, cholesterol lowering drug, antimalarial, antiepileptic, antihelminthic, agent for smoking cessation, cough suppressant, expectorant, mucolytic, nasal decongestant, dopaminergic, gastrointestinal agent, muscle relaxant, neuromuscular blocker, parasympathomimetic, prostaglandin, stimulant, anorectic, thyroid or antithyroid agent, hormone, antimigrane agent, antiobesity, and/or nonsteroidal anti-inflammatory agent. Further, the pharmaceutical agent may be one or more of the following: dihydroergotamine, fentanyl, sufentanil, lidocaine, alfentanil, lofentanil, carfentanil, pentobarbital, buspirone, ergotamine, bisphosphonate, alendronic acid, nalbuphine, bupropion, metformin, diethylcarbamazine, tramadol, heparin or a heparin derivative, amoxicillin, gabapentin, econazole, aspirin, prostaglandin, methylsergide, ergonovine, endorphins, enkephalins, oxytocin, opiates, heparin and its derivatives, clorazepic acid, barbiturate, albuterol, atropine, scopolamine, selegiline, timolol, nicotine, cocaine, novocaine, amphetamines, caffeine, methylphenidate, chlorpromazine, ketamine, epinephrine, estropipate, naloxone, naltrexone, furosemide, labetalol, metoprolol, nadolol, isoproterenol, terbutaline, sumatriptan, bupivacaine, prilocalne, loratadine, chlorpheniramine, clonidine, or tetracaine. In one example, the pharmaceutical agent is nicotine.

In certain embodiments of the present invention, the pharmaceutical composition further contains a buffering agent, colorant, flavoring, solvent, co-solvent, coating agent, binder, diluent, carrier, disintegrant, glident, lubricant, opacifying agent, humectant, granulating agent, gelling agent, polishing agent, suspending agent, sweetening agent, anti-adherent, preservative, emulsifying agent, antioxidant, levigating agent, plasticizer, surfactant, tonicity agent, viscosity agent, enteric agent, enteric coating, controlled-release agent or coating, wax, wetting agent, thickening agent, suppository base, stiffing agent, stabilizing agent, solubilizing agent, sequestering agent, ointment base, oleaginous vehicle, film-forming agent, essential oil, emollient, dissolution enhancer, dispersing agent, or cryoprotectant or combination thereof. Examples of buffering agents include phosphates, carbonates, tartrates, borates, citrates, acetates, and maleates.

In the present invention, the composition may be prepared as a buccal tablet, sublingual tablet, oral capsule, oral tablet, nasal spray, buccal or vaginal spray, liquid/semisolid, aerosol for nasal, buccal or pulmonary delivery, patch, lozenge, gum, lollypop, film, strip, paper, suppository, or pessary dosage form.

In the present invention, when the pharmaceutical composition is dissolved in water, has a pH of about physiological pH of a target mucosal membrane.

The present invention further provides a method for transmucosal delivery of an ionizable pharmaceutical agent The method includes the following steps: admixing an ionizable pharmaceutical agent with a one or more complementary lipophilic species to form a lipophilic association (LA); formulating the LA in a transmucosal dosage form; and administering the transmucosal dosage form to a targeted mucosal membrane in order to deliver the pharmaceutical agent through the mucosal membrane and into systemic circulation. The admixing step of the present invention is performed under conditions such that the ionizable pharmaceutical agent hydrogen-bonds with the complementary lipophilic species, or ionizable pharmaceutical agent ion-pairs with the complementary lipophilic species. The method of the present invention may also include the step of solubilizing the LA with a solvent having a dielectric constant less than that of water to form a solubilized LA. Examples of solvents that may be used in the present method include ethanol, ethyl acetate, isopropyl alcohol, triacetin, triethyl citrate, tributyl citrate, polyethylene glycol, propylene glycol, bisabolol, glycerin, mineral oil, ethyl oleate, fatty acid esters, squalane, animal oil, vegetable oil, hydrogenated vegetable oil, isopropyl myristate, isopropyl palmitate, glycofurol, terpene, essential oil, alcohol, polyol, and/or a silicone fluid.

The transmucosal dosage form may further include a carrier, wherein the LA, or solubilized LA, is adsorbed or absorbed to the carrier. Examples of carriers include silica or silicified microcrystalline cellulose. The transmucosal dosage form may further include a water-soluble excipient. The excipient may possess a dielectric constant less than the dielectric constant of water. Examples of suitable water-soluble excipients are sugars, polyols, alcohols, saccharides, polysaccharides, glycerin, propylene glycol, ethanol, isopropyl alcohol, ethyl acetate, triacetin, triethyl citrate, tributyl citrate, dextrates, dextrins, dextrose, fructose, lactitol, lactose, erythritol, maltose, maltitol, maltodextrins, polydextroses, trehalose, mannitol, polyethylene glycols, sorbitol, sucrose and/or xylitol.

In the present invention, the molar ratio of lipophilic species to ionizable pharmaceutical agent is at least about 1:1. In one embodiment, the pharmaceutical agent possesses a basic functional group and the lipophilic species is an acid. In the present invention, the lipophilic species is a fatty acid, a long-chain alkyl sulfonic acid, or a long-chain alkyl sulfuric acid. Examples of long-chain alkyls that are found in the fatty acid, sulfonic acid or sulfuric acid are caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic acid.

In an alternative, the pharmaceutical agent possesses an acidic functional group and the lipophilic species is a base. In certain embodiments, the lipophilic species is a amine or amide, such as cetrimide, oleamidopropyl dimethylamine, didecyldimethyl ammonium chloride, a quaternary surfactant, cetylpyridinium chloride, hexetidine, benzalkonium chloride or an amine or amide of caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic or clupanadonic acid.

In certain embodiments of the present invention the carrier is capable of forming an inclusion complex with the LA or solubilized LA. The pharmaceutical composition of the present invention may further contain a carrier, wherein the LA, or solubilized LA, is adsorbed or absorbed to the carrier. The carrier may be, for example a silica or a silicified microcrystalline cellulose.

In certain embodiments of the present invention, the pharmaceutical agent may be one or more of the following: a antihypertensive agent, analgesic, antidepressant, opioid agonist, anesthetic, antiarrhythmic, antiarthritic, antispasmodic, ACE inhibitor, decongestant, antibiotic, antihistamine, anti-anginal, diuretic, anti-hypotensive agents, anti-Parkinson agent, bronchodilator, oxytocic agent, antidiuretic, anti-hyperglycemic, antineoplastic and/or immunosuppresent agent, antiemetic, anti-infective, antifungal, antiviral, antimuscarinic, antidiabetic agent, antiallergy agent, anxiolytic, sedative, antipsychotic, bone modulating agent, cardiovascular agent, cholesterol lowering drug, antimalarial, antiepileptic, antihelminthic, agent for smoking cessation, cough suppressant, expectorant, mucolytic, nasal decongestant, dopaminergic, gastrointestinal agent, muscle relaxant, neuromuscular blocker, parasympathomimetic, prostaglandin, stimulant, anorectic, thyroid or antithyroid agent, hormone, antimigrane agent, antiobesity, and/or nonsteroidal anti-inflammatory agent. Further, the pharmaceutical agent may be one or more of the following: dihydroergotamine, fentanyl, sufentanil, lidocaine, alfentanil, lofentanil, carfentanil, pentobarbital, buspirone, ergotamine, bisphosphonate, alendronic acid, nalbuphine, bupropion, metformin, diethylcarbamazine, tramadol, heparin or a heparin derivative, amoxicillin, gabapentin, econazole, aspirin, prostaglandin, methylsergide, ergonovine, endorphins, enkephalins, oxytocin, opiates, barbiturate, albuterol, atropine, scopolamine, selegiline, timolol, nicotine, cocaine, novocaine, amphetamines, caffeine, heparin and its derivatives, clorazepic acid, methylphenidate, chlorpromazine, ketamine, epinephrine, estropipate, naloxone, naltrexone, furosemide, labetalol, metoprolol, nadolol, isoproterenol, terbutaline, sumatriptan, bupivacaine, prilocalne, loratadine, chlorpheniramine, clonidine, or tetracaine. In one embodiment the pharmaceutical agent is nicotine.

In embodiments of the present invention, the transmucosal dosage form may additionally contain a buffering agent, colorant, flavoring, solvent, co-solvent, coating agent, binder, diluent, carrier, disintegrant, glident, lubricant, opacifying agent, humectant, granulating agent, gelling agent, polishing agent, suspending agent, sweetening agent, anti-adherent, preservative, emulsifying agent, antioxidant, levigating agent, plasticizer, surfactant, tonicity agent, viscosity agent, enteric agent, enteric coating, controlled-release agent or coating, wax, wetting agent, thickening agent, suppository base, stiffing agent, stabilizing agent, solubilizing agent, sequestering agent, ointment base, oleaginous vehicle, film-forming agent, essential oil, emollient, dissolution enhancer, dispersing agent, or cryoprotectant or combination thereof.

In the method of the present invention, the buffering agent may be a phosphate, carbonate, tartrate, borate, citrate, acetate, and/or maleate.

The target mucosal tissue may be oral mucosa, esophagus, gastrointestinal tract, lungs, rectum, sinuses, eye, urinary tract or a lining of a female reproductive organ. In the method of the present invention, the ionizable pharmaceutical agent is delivered rapidly across the mucosal membrane. For example, the ionizable pharmaceutical agent is delivered across the mucosal membrane in about 10 minutes or less.

In the present invention, the pharmaceutical composition when dissolved in water has a pH near the physiological pH of the target mucosal membrane.

The present invention also provides a method of manufacturing a transmucosal pharmaceutical unit dosage forms described above. The manufacturing method involves the following steps: admixing an ionizable pharmaceutical agent with a one or more complementary lipophilic species to form a lipophilic association (LA); and formulating the LA into a transmucosal unit dosage form. The admixing is performed under conditions such that the ionizable pharmaceutical agent hydrogen-bonds, or ion-pairs, with the complementary lipophilic species. The method may further involve admixing an adsorbent, a water-soluble excipient, a disintegrant and a lubricant. In one example, the water soluble excipient is mannitol, the disintegrant is sodium starch glycolate and the lubricant is sodium stearyl fumarate.

In certain embodiments, the LA is formed into a buccal tablet, sublingual tablet, oral capsule, oral tablet, nasal spray, buccal or vaginal spray, liquid/semisolid, aerosol for nasal, buccal or pulmonary delivery, patch, lozenge, gum, lollypop, film, strip, paper, suppository, or pessary dosage form. The dosage forms may be manufactured by direct tablet compression, wet or dry granulation, dry powder blends, molding, spray-congealing, powder layering, tableting, encapsulating, spray-drying, spheronization, triturates, lyophilization, freeze drying, co-melt, microencapsulation, troching, pelleting, aerosolizing, liquid or semisolid processes manufacturing.

The present manufacturing method may further involve solubilizing the LA with a solvent having a dielectric constant less than that of water to form a solubilized LA. Examples of solvents include one or more of the following: ethanol, ethyl acetate, isopropyl alcohol, triacetin, triethyl citrate, tributyl citrate, polyethylene glycols, propylene glycol, bisabolol, glycerin, mineral oil, ethyl oleate, fatty acid esters, squalane, animal oils, vegetable oils, hydrogenated vegetable oils, isopropyl myristate, isopropyl palmitate, glycofurol, terpenes, essential oils, alcohols, polyols, and/or silicone fluids.

The present manufacturing method may further involve admixing a carrier with the LA (or solubilized LA), wherein the LA (or solubilized LA) is adsorbed or absorbed to the carrier. Examples of carriers include a silica or a silicified microcrystalline cellulose. In the present invention, the transmucosal dosage form may further contain a water-soluble excipient. Such a water-soluble excipient may possess a dielectric constant less than the dielectric constant of water. Examples of water-soluble excipients include a sugar, a polyol, an alcohol a saccharide, a polysaccharide, glycerin, propylene glycol, ethanol, isopropyl alcohol, ethyl acetate, triacetin, triethyl citrate, tributyl citrate, a dextrate, a dextrin, dextrose, fructose, lactitol, lactose, erythritol, maltose, maltitol, a maltodextrin, a polydextrose, trehalose, mannitol, a polyethylene glycol, sorbitol, sucrose and/or xylitol. In the present invention, the molar ratio of lipophilic species to ionizable pharmaceutical agent is at least about 1:1. In one embodiment, the pharmaceutical agent possesses a basic functional group and the lipophilic species is an acid. In the present invention, the lipophilic species is a fatty acid, a long-chain alkyl sulfonic acid, or a long-chain alkyl sulfuric acid. Examples of long-chain alkyls that are found in the fatty acid, sulfonic acid or sulfuric acid are caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic acid.

In certain embodiments of the present method, the pharmaceutical agent possesses an acidic functional group and the lipophilic species is a base. In certain embodiments, the lipophilic species is a amine or amide, such as cetrimide, oleamidopropyl dimethylamine, didecyldimethyl ammonium chloride, a quaternary surfactant, cetylpyridinium chloride, hexetidine, benzalkonium chloride or an amine or amide of caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic acid.

In the present method, the carrier is capable of forming an inclusion complex with the LA or solubilized LA. The pharmaceutical composition of the present invention may further contain a carrier, wherein the LA, or solubilized LA, is adsorbed or absorbed to the carrier. The carrier may be, for example a silica or a silicified microcrystalline cellulose.

Examples of pharmaceutical agents that may be used in the present method include one or more of the following: a antihypertensive agent, analgesic, antidepressant, opioid agonist, anesthetic, antiarrhythmic, antiarthritic, antispasmodic, ACE inhibitor, decongestant, antibiotic, antihistamine, anti-anginal, diuretic, anti-hypotensive agents, anti-Parkinson agent, bronchodilator, oxytocic agent, antidiuretic, anti-hyperglycemic, antineoplastic and/or immunosuppresent agent, antiemetic, anti-infective, antifungal, antiviral, antimuscarinic, antidiabetic agent, antiallergy agent, anxiolytic, sedative, antipsychotic, bone modulating agent, cardiovascular agent, cholesterol lowering drug, antimalarial, antiepileptic, antihelminthic, agent for smoking cessation, cough suppressant, expectorant, mucolytic, nasal decongestant, dopaminergic, gastrointestinal agent, muscle relaxant, neuromuscular blocker, parasympathomimetic, prostaglandin, stimulant, anorectic, thyroid or antithyroid agent, hormone, antimigrane agent, antiobesity, and/or non-steroidal anti-inflammatory agent. Further examples of pharmaceutical agents that may be used in the present method include one or more of the following: dihydroergotamine, fentanyl, sufentanil, lidocaine, alfentanil, lofentanil, carfentanil, pentobarbital, buspirone, ergotamine, bisphosphonate, alendronic acid, nalbuphine, bupropion, metformin, diethylcarbamazine, tramadol, heparin or a heparin derivative, amoxicillin, gabapentin, econazole, aspirin, prostaglandin, methylsergide, ergonovine, endorphins, enkephalins, oxytocin, opiates, barbiturate, albuterol, atropine, scopolamine, selegiline, timolol, nicotine, cocaine, novocaine, amphetamines, caffeine, heparin and its derivatives, clorazepic acid, methylphenidate, chlorpromazine, ketamine, epinephrine, estropipate, naloxone, naltrexone, furosemide, labetalol, metoprolol, nadolol, isoproterenol, terbutaline, sumatriptan, bupivacaine, prilocalne, loratadine, chlorpheniramine, clonidine, or tetracaine. In one embodiment, the pharmaceutical agent is nicotine.

In certain embodiments of the present method, the process involves admixing with the LA or solubilized LA a buffering agent, colorant, flavoring, solvent, co-solvent, coating agent, binder, diluent, carrier, disintegrant, glident, lubricant, opacifying agent, humectant, granulating agent, gelling agent, polishing agent, suspending agent, sweetening agent, anti-adherent, preservative, emulsifying agent, antioxidant, levigating agent, plasticizer, surfactant, tonicity agent, viscosity agent, enteric agent, enteric coating, controlled-release agent or coating, wax, wetting agent, thickening agent, suppository base, stiffing agent, stabilizing agent, solubilizing agent, sequestering agent, ointment base, oleaginous vehicle, film-forming agent, essential oil, emollient, dissolution enhancer, dispersing agent, or cryoprotectant or mixture thereof.

In certain embodiments of the present invention, the buffering agent is a phosphate, carbonate, tartrate, borate, citrate, acetate, and/or maleate.

In certain embodiments of the present invention, the pharmaceutical composition, when solubilzed in water, has a pH of about physiological pH of a target mucosal membrane.

Further, the present invention provides pharmaceutical products prepared by the methods of manufacture described above.

The present invention also provides a method of treating a patient in need thereof by administering a pharmaceutical composition containing an ionizable pharmaceutical agent and a one or more complementary lipophilic species, wherein the ionizable pharmaceutical agent and the one or more complementary lipophilic species are formulated in a transmucosal dosage form, and wherein the pharmaceutical composition is administered as a bolus release across a mucosal membrane. In an embodiment of this method, the ionizable pharmaceutical agent is delivered rapidly across the mucosal membrane, such as in about 10 minutes or less. In one embodiment, the ionizable pharmaceutical agent is nicotine. In one embodiment, the pharmaceutical composition is has a pH of about physiological pH of a target mucosal membrane. For example, in one embodiment nicotine is transmucosally delivered sublingually at a pH between about 5.5 and about 7.5.

DESCRIPTION OF THE INVENTION

Figure 1:
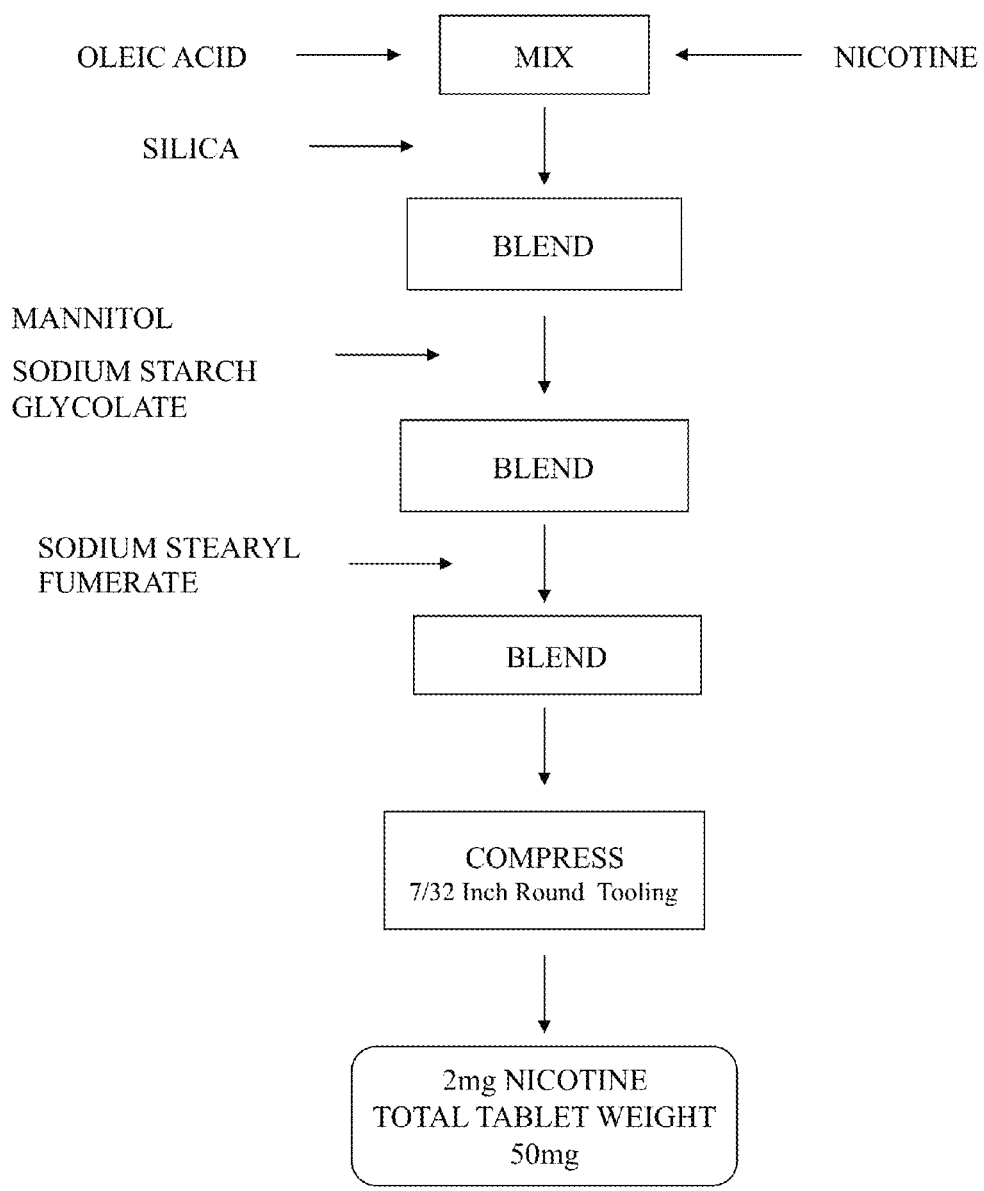
FIG. 1 is a schematic showing a method of manufacture of a nicotine sublingual/buccal tablet according to the invention.

The invention provides a composition and a method for delivery of a pharmaceutical agent. In particular, the invention provides a pharmaceutical formulation for enhanced transmucosal delivery of an ionizable pharmaceutically active substance at or near physiological pH. Transmucosal delivery includes the oral mucosa, esophagus, gastrointestinal tract including the stomach and colon, lungs, rectum, sinuses, eyes, urinary tract and the linings of the female reproductive organs. The physiological pH of these various membranes varies considerably. The physiological pH of the gastrointestinal tract increases along its length from about pH 1 in the stomach to pH 8 in the colon. Saliva has a pH around 6.8. The pH of nasal fluids range from about pH 5.5 to 6.5. The pH of the vagina is around 4.5. The invention is designed to provide transmucosal delivery in the pH range specific to the target mucosal tissue to avoid local irritation. Transmucosal absorption, as embodied in this invention, is not dependent on pH. This is unlike the prior art that requires that the pH be adjusted, typically by the use of buffers, to insure that the ionizable pharmaceutical agent is predominately in its freebase or free acid form for optimal transmucosal delivery. Transmucosal delivery of the ionizable pharmaceutical, as embodied in this invention, only requires the development of a hydration and dielectric gradient. The present invention comprises a pharmaceutical formulation that is capable of rapidly delivering a pharmaceutical agent into the mucosal tissue or the through the mucosal tissue into the circulatory system. For example the pharmaceutical agent may be absorbed through the oral mucosal tissue for systemic delivery.

The invention further provides a process for the production, and a method of use, of such a formulation. More specifically, the invention provides a high thermodynamic activity lipophilic association (LA) of an ionizable pharmaceutical agent paired with a lipophilic agent having ionic character opposite to that of the pharmaceutical agent, such that the association is a liquid or is solubilized in a lower-than-water dielectric solvent. As used herein, the term "high thermodynamic activity" means that the lipophilic association or lipophilic association solvate is in a liquid state at room temperature. The LA being a liquid state, or solubilized, is at high thermodynamic activity such that drug dissolution is no longer rate limiting to transmucosal absorption. Further, the invention provides for formulating the high thermodynamic activity LA into a lower-than-water dielectric dosage form, which upon hydration results in an increasingly higher dielectric gradient. This provides the driving force for enhanced delivery of the lipophilized ionizable pharmaceutical agent through the mucus and into systemic circulation at or near physiological pH.

The invention provides, inter alia, a process for making a transmucosal drug delivery system for an ionizable pharmaceutical agent by use of a lipophilic species having a charge, when ionized, opposite that of the ionized pharmaceutical agent. It is the applicants present understanding that a lipophilic association according to the invention may be, for example, prepared according to the outline below. That is, for a basic ionizable functional group on an ionizable pharmaceutical agent that is not ionized (deprotonated), the corresponding acidic lipophilic species is also not ionized (protonated). For a basic ionizable group on a ionizable pharmaceutical agent that is ionized (protonated), the corresponding acidic lipophilic species is also ionized (deprotonated). In like manner, for an acid ionizable functional group on an ionizable pharmaceutical agent that is not ionized (protonated), the corresponding basic lipophilic species is also not ionized (deprotonated). For an acid ionizable group on a ionizable pharmaceutical agent that is ionized (deprotonated), the corresponding basic lipophilic species is also ionized (protonated).

For a basic drug, a lipophilic species according to the invention is, for example, fatty acid or another lipophilic species. For a basic drug, a lipophilic species according to the invention may, for example, be one or more of the following fatty acids, or long-chain alkyl sulfonic acids, or a long-chain alkyl sulfuric acids: caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic.

For an acidic drug, a lipophilic species according to the invention is, for example, a fatty amine or another lipophilic species. For an acidic drug, a lipophilic species according to the invention is cetrimide, oleamidopropyl dimethylamine, didecyldimethyl ammonium chloride, quaternary surfactants, cetylpyridinium chloride, hexetidine, benzalkonium chloride and the following fatty amines and acid amides: caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic.

A formulation according to the invention contains an ionizable drug and an oppositely charged lipophilic species, to form the lipophilic association. The LA may require, if not already at a high thermodynamic activity liquid state, the use of lower-than-water dielectric solvent in order to prepare a LA-solvate that has high thermodynamic activity. Examples of appropriate lower-than-water dielectric solvents include ethanol, ethyl acetate, isopropyl alcohol, triacetin, triethyl citrate, tributyl citrate, polyethylene glycols, propylene glycol, bisabolol, glycerin, mineral oil, ethyl oleate, fatty acid esters, squalane, animal oils, vegetable oils, hydrogenated vegetable oils, isopropyl myristate, isopropyl palmitate, glycofurol, terpenes, essential oils, alcohols, polyols, or silicone fluids.

A formulation according to the invention contains an ionizable drug, an oppositely charged lipophilic species, and an excipient, for example, a water-soluble excipient, to lower the local delivery area's dielectric constant, which is more favorable for association between the pharmaceutical agent and the lipophilic species in this lipophilic association. Examples of appropriate water-soluble excipients include a sugar, a polyol, an alcohol, a saccharide, a polysaccharide, glycerin, propylene glycol, ethanol, isopropyl alcohol, ethyl acetate, triacetin, triethyl citrate, tributyl citrate, a dextrate, dextrin, dextrose, fructose, lactitol, lactose, erythritol, maltose, maltitol, maltodextrin, polydextrose, trehalose, mannitol, polyethylene glycol, sorbitol, sucrose and/or xylitol.

While the invention is not to be limited by theory, it is the applicant's understanding that, as water from the local delivery environment hydrates the high thermodynamic activity, lipophilic association, lower-than-water dielectric formulation according to the invention, a hydration and dielectric gradient is formed that provides the driving force for delivery of the lipophilized ionizable pharmaceutical agent through the mucosa and into systemic circulation.

Surprisingly, it has been found that, in one embodiment, i.e., a nicotine sublingual/buccal tablet, a tablet containing a LA prepared with nicotine and oleic acid at a 1:1 molar ratio is effective in providing a rapid, bolus dose of nicotine after sublingual administration. In the art, to enhance delivery, many formulations require a molar ratio of oppositely charged species to active pharmaceutical agent of 50:1 or greater (M. Trotta, E. Urazio, E. Peira and C. Pulitano, "Influence of ion pairing on topical delivery of retinoic acid from microemulsions", J. Control Release, 2003, Vol. 86, pp 315-321).

Further, in a nicotine sublingual/buccal tablet embodiment of the invention prepared with nicotine and oleic acid, the LA is a liquid with a pH in water of about 5.5 to 7.5, depending on the amount of the oleic acid present. Delivery is as rapid, and possibly more rapid, at lower pHs, the acidity being determined by any excess oleic acid over that needed for formation of the LA. However, excessive acidity is not necessary. Lower-than-physiological pHs would result if excessive amounts of oleic acid were needed for transmucosal delivery of the ionizable pharmaceutical agent. This attests to the efficiency of the invention. Further, at the pH range of this delivery system, nicotine predominately in the ionized form. Such efficient delivery at a pH where nicotine is ionized is surprising, because ionized pharmaceutical agents typically have very poor transmucosal delivery (Beckett and Hossie: Buccal Absorption of Drugs, in Handbook of Experimental Pharmacology, ed. B. B. Brodie and J. R. Gillette; Springer-Verlag, Berlin (1971), Ch. 3, and H. R. Leipold and E. Quadros: Nicotine Permeation Through Buccal Cultures, in Proceed. Intern. Symp. Control. Rel. Bioact. Mater., Controlled Release Society, 20 (1993), 242-243).

When a nicotine formulation is prepared according to the present invention, a rapid, bolus delivery of nicotine results from sublingual administration of the formulation in the physiological pH range of saliva, where nicotine's predominant form is ionized. This is among the advantages that a formulation according to the invention possesses over other known formulations. In general, transmucosal and transdermal drug delivery systems for ionizable pharmaceutical agents resort to using the free-base or free-acid form of the drug to obtain the desired level of drug permeation. Delivery of the free-base or free-acid form can cause the local delivery area's pH to be far outside the normal range of the local delivery area's customary physiological pH. This pH perturbation can result in local tissue irritation and cell death. By virtue of the inherent capacity of a formulation according to the invention to deliver ionizable pharmaceutical agents at or near physiological pH, delivery of a ionizable pharmaceutical agent according to the invention significantly reduces local tissue irritation and cell death when compared with delivery of other formulations. For example, delivery of nicotine free-base could cause a transient increase in local delivery area pH to 10 or above, a pH known in the art to be caustic. Indeed, one of the side effects of the sublingual nicotine tablet MICROTAB' is an oral ulcer in the delivery area.

Transmucosal drug delivery according to the invention includes inter alia certain preparative steps. According to the invention, an ionizable pharmaceutical agent is prepared into a lipophilic association (LA) by pairing with a lipophilic species that bears, when ionized, an opposite charge to that of the ionized pharmaceutical agent. In selecting the lipophilic species, efforts are made to ensure that the LA is at high thermodynamic activity, i.e. produces a liquid at room temperature. If this is not possible the LA is solvated in a lower-than-water dielectric solvent to produce a high activity, liquid LA-solvate. Further, the LA or LA-solvate is formulated so that when placed in water results in a solution pH at or near physiological pH of the targeted mucosal tissue. The LA or LA-solvate is formulated into a dosage form that on contact with water results in an increasing hydration and dielectric gradient, providing a driving force for transmucosal delivery of the lipophilized ionizable pharmaceutical agent. This can be accomplished by including a water-soluble excipient that has a lower dielectric constant than water or that, when solubilized in water, lowers the solution's dielectric constant from that of water.

The invention possesses a number of advantages over known formulations. The invention's lipophilic, high thermodynamic activity LA formulations provide for improved transmucosal drug absorption. First, dissolution of the pharmaceutical agent is no longer rate limiting to transmucosal absorption, i.e. the ionizable pharmaceutical agent is already dissolved being a liquid or in solution as the LA or LA-solvate respectively. Second, being in a liquid state the LA is at high molecular thermodynamic activity. Third, due to the lipophilic species used in the formation of the LA, it has greater affinity to lower-than-water dielectric environments such as cell membranes. The combination of a high thermodynamic activity liquid state, with the drug being in solution so as dissolution is not rate limiting, and the lipophilicity of the LA, driven by development of an increasing hydration and dielectric gradient as water enters the lower-than-water dielectric dosage form, provides optimal conditions for delivery of an ionizable pharmaceutical agent through the mucosa and into systemic circulation. A further advantage that the invention provides is transmucosal drug delivery at or near physiological pH. Previously known transmucosal delivery systems for ionizable pharmaceutical agents resort to using the free-base or free-acid forms of the drug substance to provide transmucosal drug permeation. In such cases the local delivery area pH can be far outside the range of physiological pH, resulting in local tissue irritation and cell death.

A formulation according to the invention is embodied in any of a wide variety of different dosage forms, such as buccal tablet, sublingual tablet, oral capsule, oral tablet, nasal spray, buccal or vaginal spray, liquid/semisolid, aerosol for nasal, buccal or pulmonary delivery, patch, lozenge, gum, lollypop, film, strip, paper, suppository, pessary or other dosage forms using manufacturing techniques familiar to one versed in the art of formulating and processing pharmaceutical dosage forms. A manufacturing technique according to the invention includes any of the processes of direct tablet compression, wet or dry granulation, co-melt, dry powder blends, molding, spray-congealing, powder layering, tableting, encapsulating, spray-drying, spheronization, triturates, lyophilization, freeze drying, microencapsulation, troching, pelleting, aerosolizing, liquid or semisolid preparation.

In one embodiment of the present invention, a process of direct powder blends is used to create a solid dosage form. The process of direct powder blends can be outlined as weighing and blending of several ingredients and either encapsulating or compressing the blend into tablet. This is the process that is used in the examples given herein as embodiments.

In one embodiment of the present invention, a process of wet granulation is used to create a solid dosage form. The process of wet granulation can be outlined as several steps: weighing and blending of several ingredients in the presence of solvent(s), drying the mixture into a solid, and milling the solid to proper size.

In the weighing and blending step of wet granulation, proper amounts of drug and lipophilic species and solvent are mixed thoroughly. Additional ingredients may be added to facilitate the mixing of the ingredients. The end result of this step is a finely blended mixture in which the drug and the lipophilic agent are mixed.

In another embodiment of the present invention, a process of co-melting is used. In this process, the LA is heated with a low melting water-soluble excipient, e.g. polyethylene glycol 6000. In its melted state, the excipient can act as a solvent into which the LA is dissolved or dispersed. The mixture of LA and excipient is then cooled and solidified. The solid solution of LA and excipient will be further processed into compressible powder. Other ingredients may also be added to the co-melted powder to complete the drug formulation.

In yet another embodiment of the present invention, a process of freeze-drying is used. In this process, the LA is dissolved or dispersed in water with a water-soluble powder, e.g. mannitol. The solution is quickly frozen. The frozen solid is then put into a vacuum chamber where the water is removed from the solid via sublimation. The resulting powder is a solid carrier of LA on a water-soluble excipient.

In yet another embodiment of the present invention, a process of spray drying is used. In this process, the LA is dissolved or dispersed in a solvent with an excipient. The solution or dispersion is then sprayed into a chamber. The solvent is evaporated while the droplets are in the air. The result is a fine powder consisting of the LA on carrier excipient.

There are many other processes for making the final dosage form. The selection of the process will mainly depend on the LA or LA-solvate and the final dosage form most suitable for treatment of the diseased state.

One embodiment of the invention provides a rapid, bolus dose of an ionizable pharmaceutical agent transmucosally and is formulated as liquid/semisolid or as a rapidly dissolving dosage form. Further embodiments of the invention provides sustained, delayed and pulsatile drug delivery. In the case of rapid bolus administration, the dosage form dissolves and releases the ionizable pharmaceutical agent relatively quickly, such as within 30 minutes. A sustained release formulation provides a slower delivery of the ionizable pharmaceutical agent from the dosage form. A delayed release dosage form provides a period of time after administration in which no drug delivery occurs, e.g., enteric or colonic delivery systems. A pulsatile release formulation provides repeated bolus delivery of the ionizable pharmaceutical agent from the dosage form. Given the description of the invention contained in this application, it will be apparent to one skilled in the art how to prepare any such dosage form.

To treat a subject, the formulation, is administered by oral, sublingual, buccal, vaginal, rectal, pulmonary, ophthalmic, or intranasal route. Formulations will contain an effective amount of the active ingredient in a LA or LA-solvate. The effective amount is sufficient to treat a disease state in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject. The quantity also depends upon the degree of activity desired. Effective dosages can be readily established by one of ordinary skill in the art through routine trials establishing dose response curves. The subject is treated by administration of the formulation in one or more doses. Multiple doses may be administered as required.

Intranasal formulations may include vehicles that neither cause irritation to the nasal mucosa nor significantly disturb ciliary function. Diluents such as propylene glycol or polyethylene glycol or other known substances can be employed with the subject invention. The nasal formulations may also contain preservatives such as, but not limited to, chlorobutanol and benzalkonium chloride.

Oral preparations may be in the form of, for example, aqueous solution using excipients to lower dielectric constant to less than water or oily suspension, solutions, emulsions, syrups or elixirs, or may be presented dry in tablet or capsule form or a product for reconstitution with water or other suitable vehicle before use. Such liquid preparations may contain conventional additives such as suspending agents, emulsifying agents, lower-than-water dielectric excipients, non-aqueous vehicles (which may include edible oils), or preservative.

Ionizable Pharmaceutical Agent. A pharmaceutical agent according to the invention is an ionizable drug substance used for diagnosis, prevention, control, or treatment of a physiological, pathological or psychological condition. It is understood that a considerable variety of drug classes and specific drugs are useful as a pharmaceutical agent according to the invention. A pharmaceutical agent according to the invention may be, for example, a member of any of the following classes of drugs: antihypertensive agents, analgesics, antidepressants, opioid agonist, anesthetics, antiarrhythmic, antiarthritics, antispasmodics, ACE inhibitors, decongestants, antibiotics, antihistamines, anti-anginal, diuretics, anti-hypotensive agents, anti-Parkinson agents, bronchodilators, oxytocic agents, anti-diuretics, anti-hyperglycemics, antineoplastics and immunosuppresents agents, antiemetics, anti-infectives, antifungals, antivirals, antimuscarinics, antidiabetic agents, antiallergy agents, anxiolytics, sedatives, antipsychotics, bone modulating agents, cardiovascular agents, cholesterol lowering drugs, antimalarials, antiepileptics, antihelmintics, agents for smoking cessation, cough suppressants, expectorants, mucolytics, nasal decongestants, dopaminergics, gastrointestinal agents, muscle relaxants, neuromuscular blockers, parasympathomimetics, prostaglandins, stimulants, anorectics, thyroid and antithyroid agents, hormones, antimigrane agents, antiobesity, and non-steroidal anti-inflammatory agents. In an embodiment, a pharmaceutical agent according to the invention is a dihydroergotamine, fentanyl, sufentanil, lidocaine, alfentanil, lofentanil, carfentanil, pentobarbital, buspirone, ergotamine, bisphosphonates, alendronic acid, nalbuphine, bupropion, metformin, diethylcarbamazine, tramadol, amoxicillian, gabapentin, econazole, aspirin, heparin and its derivatives, prostaglandins, methylsergide, ergonovine, endorphin, enkephalins, oxytocin, opiate, barbituates, albuterol, atropine, scopolamine, selegiline, timolol, nicotine, cocaine, novocaine, amphetamine, caffeine, clorazepic acid, methylphenidate, chlorpromazine, ketamine, epinephrine, estropipate, naloxone, naltrexone, furosemide, labetalol, metoprolol, nadolol, isoproterenol, terbutaline, sumatriptan, bupivacaine, prilocalne, loratadine, chlorpheniramine, clonidine, and/or tetracaine.

Lipophilic Species. A lipophilic species according to the invention possesses, when ionized, a charge opposite that of an ionizable pharmaceutical agent according to the invention. A lipophilic species according to the invention combines with the pharmaceutical agent to form a high thermodynamic activity, low dielectric constant, lipophilic association. In an embodiment, a pharmaceutical agent and a lipophilic species are mixed together in about a 1:1 molar ratio. In a further embodiment, an ionizable pharmaceutical agent having more than one ionizable group may require mixing with an equal molar ratio of oppositely charged lipophilic species for each ionizable group. In yet a further embodiment, a pharmaceutical agent itself bears oppositely charged ionizable groups, such as in the case of a peptide or a protein, and may be mixed with both anionic and cationic lipophilic species. In a particular embodiment, a molar excess of a lipophilic species is mixed with the ionizable pharmaceutical agent, lowering the dielectric constant and improving solubility of the LA.

For a drug having basic functional groups, a lipophilic species according to the invention is an anion (when ionized), for example, a fatty acid. For drugs with basic functional groups, a lipophilic species according to the invention is one or more of the following fatty acids, long-chain alkyl sulfonic acids, or long-chain alkyl sulfuric acids: caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic. For drugs with acidic functional groups, a lipophilic species according to the invention is a cation (when ionized), for example, fatty amines. For drugs with acidic functional groups, a lipophilic species according to the invention is one or more of the following: cetrimide, oleamidopropyl dimethylamine, didecyldimethyl ammonium chloride, quaternary surfactants, cetylpyridinium chloride, hexetidine, benzalkonium chloride, and/or one or more of the following fatty amines and acid amides: caproic, caprylic, capric, lauric, myristic, palmitic, stearic, arachidic, behenic, lignoceric, myristoleic, palmitoleic, oleic, gadoleic, erucic, ricinoleic, linoleic, linolenic, licanic, arachidonic and/or clupanadonic. Drugs with multiple functional groups would require mixtures of these lipophilic species.

LA Solvent. A lipophilic species according to the invention is mixed with a pharmaceutical agent according to the invention to form a high thermodynamic activity, low dielectric, lipophilic LA. In an embodiment, the LA thus formed is a liquid and therefore is already at high activity. In a further embodiment, the LA is solubilized in order to attain a high activity thermodynamic state, i.e., a liquid state at room temperature. In a particular embodiment, a formulation according to the invention contains a molar excess of one or more lipophilic species for solubilizing and providing a low dielectric liquid environment for the LA. In a further particular embodiment, a formulation according to the invention contains a lower-than-water dielectric solvent other than a lipophilic species. In an embodiment, a lower-than-water dielectric solvent other than a lipophilic species according to the invention is ethanol, ethyl acetate, isopropyl alcohol, triacetin, triethyl citrate, tributyl citrate, a polyethylene glycol, propylene glycol, bisabolol, glycerin, mineral oil, ethyl oleate, a fatty acid ester, squalane, an animal oil, a vegetable oil, a hydrogenated vegetable oil, isopropyl myristate, isopropyl palmitate, glycofurol, a terepene, an essential oil, an alcohol, a polyol, or a silicone fluid.

Solid Carrier. In an embodiment, a formulation according to the invention contains a solid carrier. A liquid LA or LA-solvate according to the invention is adsorbed or absorbed onto a solid carrier to improve processing. When an ingredient is a liquid it is typically necessary to convert it into a solid before blending it with other powders to prepare tablets, capsules or other solid dosage forms. The liquid is typically of an oily nature and can be adsorbed onto the surface of a solid. Adsorption, being a surface phenomenon, is influenced by the available surface area on the solid. Thus, the most efficient adsorbents are usually very small particles. In an embodiment, an adsorbent according the invention may be microcrystalline celluloses, cellulose powder, silicified microcrystalline celluloses (PROSOLV 50, PROSOLV 90HD), silicas (ZEOPHARM 5170, AEROPERL 300, SYLOID 244FP, SYLOID 63FP, SYLOID 72 FP), clays, talc, starches, pregelatinized starches, calcium carbonate, and magnesium carbonate. In one embodiment, a solid carrier for a liquid LA according to the invention is a cyclodextrin or a substituted cyclodextrin. These materials form inclusion complexes with lipophilic molecules on a 1:1 molar ratio. Cyclodextrins are "bucket like" molecules, with a ridged structure and a central cavity. The internal surface of the central cavity is lipophilic, while the outside surface is hydrophilic. This arrangement allows the cyclodextrin to harbor a guest molecule within the cavity, forming an inclusion complex that is water-soluble. Thus, this mechanism of solidification is by absorption.

Water-Soluble Excipient. In an embodiment, a formulation according to the invention contains a water-soluble excipient. A variety of excipients are useful as the water-soluble component of the invention, the selection being based on the delivery system. In an embodiment, the water-soluble excipient can be a water-soluble LA solvent, e.g., propylene glycol for use in a liquid dosage form. In an embodiment, the water-soluble excipient can be a tablet diluent, e.g., mannitol for a solid dosage form. The development of a gradually increasing hydration and dielectric gradient in the dosage form is most favorable for transmucosal delivery of an ionizable pharmaceutical agent according to the invention. Hence, in an embodiment, a water-soluble excipient according to the invention is one or more of the following: a sugar, a polyol, a alcohol, a saccharide, a polysaccharide, glycerin, propylene glycol, ethanol, isopropyl alcohol, ethyl acetate, triacetin, triethyl citrate, tributyl citrate, a dextrate, a dextrin, dextrose, fructose (ADVANTOSE FS 95), lactitol (FINLAC DC), lactose, erythritol, maltose, maltitol, a maltodextrin, a polydextrose, trehalose, mannitol (PEARLITOL 300 DC, PEARLITOL 400 DC, PEARLITOL 500 DC, MANNOGEM 2080, MANNOGEM EZ, PARTEK M200, PARTEK M300), a polyethylene glycol, sorbitol, sucrose and xylitol (XYLITOL 200, XYLITOL 300).

Other Excipients. In an embodiment, another excipient, chosen to enhance processability, form, function or appeal of the formulation is included in a formulation according to the invention. In such an embodiment, another excipient according to the invention is a buffering agent (such as phosphate, carbonate, tartrate, borate, citrate, acetate, and maleate buffers), colorant, flavoring, solvent and co-solvent, coating agent, binder, diluent, carrier, disintegrant, glident, lubricant, opacifying agent, humectant, granulating agent, gelling agent, polishing agent, suspending agent, sweetening agent, anti-adherent, preservative, emulsifying agent, antioxidant, levigating agent, plasticizer, surfactant, tonicity agent, viscosity agent, enteric agent and coating, controlled-release agent and coating, wax, wetting agent, thickening agent, suppository base, stiffing agent, stabilizing agent, solubilizing agent, sequestering agent, ointment base, oleaginous vehicle, film-forming agent, essential oil, emollient, dissolution enhancer, dispersing agent, and/or cryoprotectant or combinations thereof.

EXEMPLARY EMBODIMENTS

Sublingual/Buccal Tablets

It will be readily understood that the components, formulations, processes, and methods of use of the present invention, as generally described herein, are arranged and designed in a wide variety of different dosage forms and formulations. Thus, the following more detailed description of the embodiments of the formulation and methods of use of the present invention is not intended to limit the scope of the present invention, as claimed, but merely represents one of the dosage form embodiments of the invention, e.g. a sublingual/buccal tablet.

Example I

Nicotine

In an embodiment, a buccal/sublingual tablet formulation according to the invention is useful in nicotine replacement therapy (NRT). Certain commercially available products for NRT in smoking cessation, such as patches, gum, and lozenges, do not provide for the rapid rise or peak nicotine plasma levels obtained by smoking. Certain other products, such as nasal sprays, inhalers, and certain sublingual tablets, that attempt to provide nicotine plasma levels similar to smoking a cigarette, result in local irritation.

Pomerleau (Ann. Behav. Med. 1998, Vol. 36, 158-163) listed criteria for a successful NRT: 1) the method should be safe and easy to use; 2) specific doses should be accurately and reproducibly delivered; 3) the pharmacokinetics should resemble those of cigarette smoking. Judging from the very limited efficacy of the current commercial NRTs (typically less than 20%), current commercial NRTs are not meeting the Pomerleau criteria.

However, an embodiment of the present invention did meet the Pomerleau criteria. One embodiment of the present invention provides a convenient, small, round sublingual/buccal tablet useful for NRT. Such a tablet rapidly dissolved under the tongue or dissolved more slowly in the buccal cavity between the gums and cheek. Further, it did not produce ulcers in the mouth, which is one of the undesired side effects of other formulations that use nicotine in its free base form. It was also convenient and easy to use and is a socially acceptable delivery system. It is much more like taking a breath mint, unlike nasal sprays or inhalers. Further, such a tablet reproducibly provided a rapid bolus of nicotine after sublingual administration. Hence a sublingual/buccal tablet according to the invention meets the Pomerleau criteria and is more successful at helping smokers quit cigarettes than the currently marketed products.

In one embodiment, the invention provided a 2 mg strength nicotine sublingual/buccal tablet having a total tablet weight around 50 mg and nominal dimensions of about 0.55 cm in diameter and a thickness of about 0.15 cm. In such an embodiment, the ionic pharmaceutical agent according to the invention contained nicotine and a lipophilic species. The lipophilic species was oleic acid. The molar ratio of lipophilic species to ionic pharmaceutical agent was not less than about 1:1. However, a molar excess of the lipophilic species, in this example oleic acid, may be used, e.g., 1.2:1, but is not limited to this ratio. This LA is a liquid at room temperature. In order to convert the LA into a flowable powder suitable for use in direct compression tableting required the use of an adsorbent/absorbent, such as silica. In order to manufacture a rapidly disintegrating, directly compressible tablet other excipients were needed. For example, the diluent may be the water-soluble, direct compression tableting excipient mannitol. A disintegrant is included to rapidly break the tablet apart upon administration. An exemplary disintegrant is sodium starch glycolate. An exemplary tablet lubricant is sodium stearyl fumarate. A quantitative formulation is given in Table I.

TABLE I 2 mg Nicotine Sublingual/Buccal Tablet Formulation

| INGREDIENT | AMOUNT (mg/tablet) |
|---|---|
| Nicotine | 2.0 |
| Oleic Acid | 3.5 |
| Silica | 4.0 |
| Mannitol | 38.5 |
| Sodium Starch Glycolate | 1.5 |
| Sodium Stearyl Fumarate | 0.5 |
| Total Tablet Weight | 50.0 |

A method of manufacture for a sublingual/buccal tablet according to the invention is a suitable method known in the art, such as the addition of the nicotine LA or LA-solvate to premanufactured tablets, cold compressions with inert fillers and binders, direct tablet compression blends, direct powder blends, wet or dry granulations, molding, lyophilization, microencapsulation, co-melt, freeze drying, spray-congealing, spray-drying, spheronization, triturates, troching, powder layering, pelleting, encapsulation. An exemplary method of manufacture is outlined below and schematically in FIG. 1.

STEP 1: Mix nicotine and oleic acid together until homogeneous, to form a nicotine LA.

STEP 2: Blend the nicotine LA with silica until homogeneous to form a nicotine LA silica carrier blend.

STEP 3: Add the nicotine LA silica carrier blend to mannitol and sodium starch glycolate and blend until homogeneous to form a further blend.

STEP 4: Add sodium stearyl fumarate to the further blend and blend until well lubricated to form a lubricated blend.

STEP 5: Compressing the lubricated blend into tablets using $7/32"$ round tooling.

Method of packaging. The sublingual/buccal tablets may be packaged in such a manner as to aid in maintaining nicotine stability. Exemplary packaging methods and materials include, but are not limited to, blister packaging in a foil/foil, foil/Acrylonitrile, foil/Polychlorotrifluoroethylene laminates.

Figure 2:
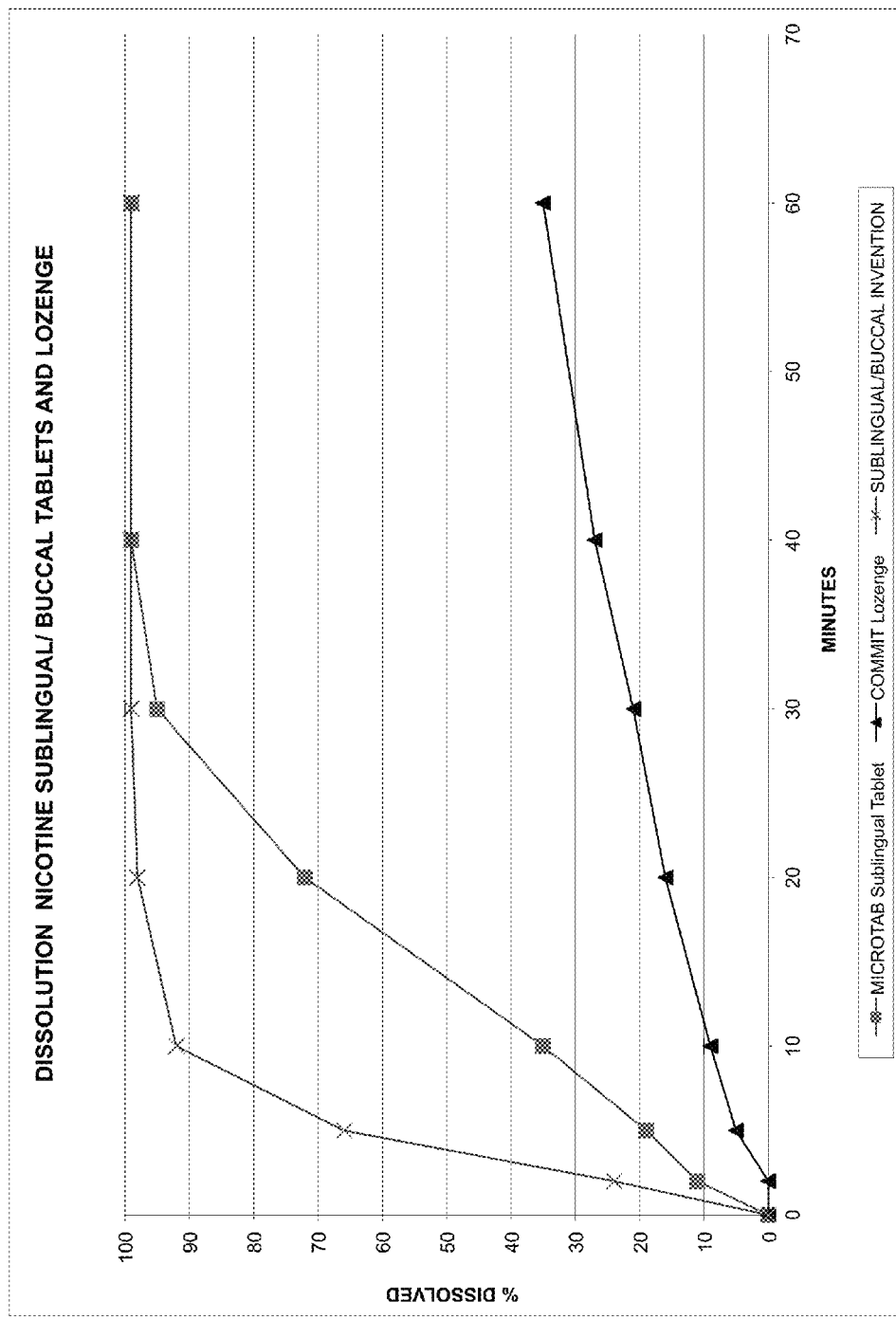
FIG. 2 is a graph showing a dissolution profile of nicotine as delivered by a formulation according to the invention and compared to a dissolution profile of prior-art formulations.

Comparative dissolution. Drug dissolution is a prerequisite to drug absorption and clinical response for almost all drugs given orally. (G. L. Amidon, H. Lennemas, V. P. Shah, J. R. Crison, "A Theoretical Basis for a Biopharmaceutical Drug Classification: The Correlation of in Vitro Drug Product Dissolution and in Vivo Bioavailability," Pharm. Res. 1995, Vol. 12, No. 3, pp 413-420.) Dissolution is considered an in vitro technique that gives good correlation to a product's in vivo performance. A drug must first be released from the delivery system in order to be available for absorption. Therefore, tablets having a faster dissolution would be expected to have faster absorption in vivo. FIG. 2 presents the dissolution results of the nicotine sublingual/buccal tablet, the embodiment of the invention as presented herein, and two nicotine commercial products, i.e., a lozenge (COMMIT™ and a sublingual tablet MICROTAB™). Dissolution was conducted in 900 ml of D.I. water at 50 RPM using USP Apparatus 2. Samples were pulled at 2, 5, 10, 20, 30, 40 and 60 minutes, and analysis was by HPLC.

As can be seen from the dissolution profiles, the sublingual/buccal tablet released over 90% of the nicotine in the tablet within 10 minutes. This rapid release of nicotine corresponded to typical plasma nicotine levels obtained from smoking a cigarette, which peak in about 10 minutes (WO 03/055486 A1). The lozenge COMMIT™ shows a very slow profile releasing only 35% of the dosage at the end of 60 minutes. The other sublingual tablet, MICROTAB™, takes about 30 minutes to reach the same level that the embodied invention given herein reached within 10 minutes, i.e., 90% of the dosage dissolved.

The other products fail to provide rapid nicotine release, and therefore cannot provide a nicotine plasma level comparable to what a person obtains from smoking a cigarette. The present invention as embodied herein did provide rapid nicotine release. Indeed, more than 90% of the nicotine in the tablet was dissolved and available for transmucosal absorption within 10 minutes. It should be noted that the pH of the dissolution media obtained after dissolution of the sublingual/buccal tablets as embodied in this invention was 6.2. This is very similar to the pH of saliva, which is general recognized as being around 6.8. At a pH of 6.8 only about 10% of the nicotine is in the free base form. Others have indicated that in order to promote absorption of nicotine through the oral mucosa, the pH of the saliva must be increased so that nicotine will be predominately in the free base form (WO 03/055486 A1). The present invention provides for nicotine transmucosal absorption in acidic conditions similar to the physiological pH of the saliva. Others indicated that such a low pH nicotine transmucosal delivery would not be efficacious.

In Vivo Data: Two male volunteers and one female volunteer, all former smokers, placed the nicotine sublingual tablet, as embodied herein, under the tongue and left it undisturbed. Immediately upon administration a tingling sensation was very apparent in the area where the sublingual tablet was placed. Shortly thereafter, i.e., within a few minutes, the physiological effects of nicotine were very apparent to all three volunteers. This included being light-headed, dizzy, a warning sensation and an increase in heart rate. In all three volunteers, the symptoms peaked within 10 minutes and the tablets were totally dissolved in less than 5 minutes. Interestingly, the usually overwhelming acrid taste of nicotine was not apparent. Instead there was a slightly bitter taste that was complimented by the sweet taste of mannitol. Within 30 minutes all volunteers felt normal. All three volunteers stated that the nicotine sublingual tablet, as embodied herein, provided a bolus of nicotine that was similar to that obtained from smoking a cigarette.

Method of Use: In an exemplary embodiment, a buccal/sublingual tablet formulation according to the invention is useful in nicotine replacement therapy (NRT). This therapy is designed to allow smokers to quit smoking by providing nicotine in a non-carcinogenic delivery system, i.e., without tars. In a typical treatment regiment, the smoker starts by placing a 2 or 4 mg nicotine sublingual tablet under the tongue and leaving it undistributed until dissolved, typically within 5 minutes, whenever there is an urge to smoke. In one embodiment, about 10 to 30 sublingual tablets are used per day. After a period of several weeks, the dosage is lowered to 2 mg or 1 mg (depending on the starting strength) then to 0.5 mg. Eventually, a placebo is used, if required. This gradual reduction in nicotine content helps wean the smoker off the desire for nicotine. This is usually supplemented with counseling. The tablets of the present invention can also be used by smokers when it is not acceptable for them to smoke, e.g., when they are in an airplane. The dosage range for this embodiment may be from 0.5 mg to 5 mg of nicotine.

Example II

Epinephrine

Epinephrine (adrenaline) is commonly given by subcutaneous or intramuscular injection for anaphylactic shock, allergic reactions and acute asthmatic attacks. The usual dosage is 300 µg, given intramuscularly by use of an auto-injector. Patients with a history of severe allergic reactions to insect bites or stings, foods, drugs, and other allergens, as well as idiopathic and exercise induced anaphylaxis, are supplied with auto-injectors for intramuscular self-administration. This is the preferred treatment for serious allergic reactions. An embodiment according to the invention, an epinephrine sublingual/buccal tablet as described below, has several advantages over the current therapy. First, the invention as embodied herein is convenient, non-invasive and painless to administer. Further, epinephrine is also unstable in light and is readily oxidized; an embodiment according to the invention, as described below, being a solid-state product rather than liquid preparation, provides better stability.

In such an embodiment, the invention provides a 300 µg strength epinephrine sublingual/buccal tablet having a total tablet weight around 50 mg and nominal dimensions of about 0.55 cm in diameter and a thickness of about 0.15 cm. In such an embodiment, the ionic pharmaceutical agent according to the invention contains epinephrine and the lipophilic species with which it is combined (such as oleic acid), the molar ratio of the lipophilic species to ionic pharmaceutical agent being not less than about 1:1. However, a molar excess of the lipophilic species, in this example oleic acid, may be used, e.g., 1.2:1. Embodiments are described herein. In certain embodiments, the LA may require the use of a solvent to stabilize or solubilize the LA, e.g., ethyl oleate and polyethylene glycol 400. Embodiments are described herein. In certain embodiments, the liquid LA or LA-solvate requires the use of an adsorbent/absorbent in order to convert it into a flowable powder suitable for use in direct compression tableting (such as silica). Other excipients are in some circumstances useful in order to manufacture a rapidly disintegrating, directly compressible tablet (such as the water-soluble, direct compression tableting excipient mannitol). In order to rapidly break the tablet apart upon administration, a disintegrant is used. In one embodiment the disintegrant is sodium starch glycolate. An exemplary tablet lubricant is sodium stearyl fumarate. Exemplary embodiments are provided in Table II.

TABLE II

300 µg Epinephrine Sublingual/Buccal Tablet Formulations

| INGREDIENT | AMOUNT (mg/tablet) Embodiment 1 | AMOUNT (mg/tablet) Embodiment 2 | AMOUNT (mg/tablet) Embodiment 3 |
|---|---|---|---|
| Epinephrine | 0.30 | 0.30 | 0.30 |
| Oleic Acid | 0.46 | 0.46 | 0.46 |
| Ethyl oleate | — | 4.74 | — |
| Polyethylene glycol 400 | — | — | 4.74 |
| Silica | 0.55 | 4.00 | 4.00 |
| Mannitol | 46.69 | 38.50 | 38.50 |
| Sodium Starch Glycolate | 1.50 | 1.50 | 1.50 |
| Sodium Stearyl Fumarate | 0.50 | 0.50 | 0.50 |
| Total Tablet Weight | 50.00 | 50.00 | 50.00 |

Figure 3:
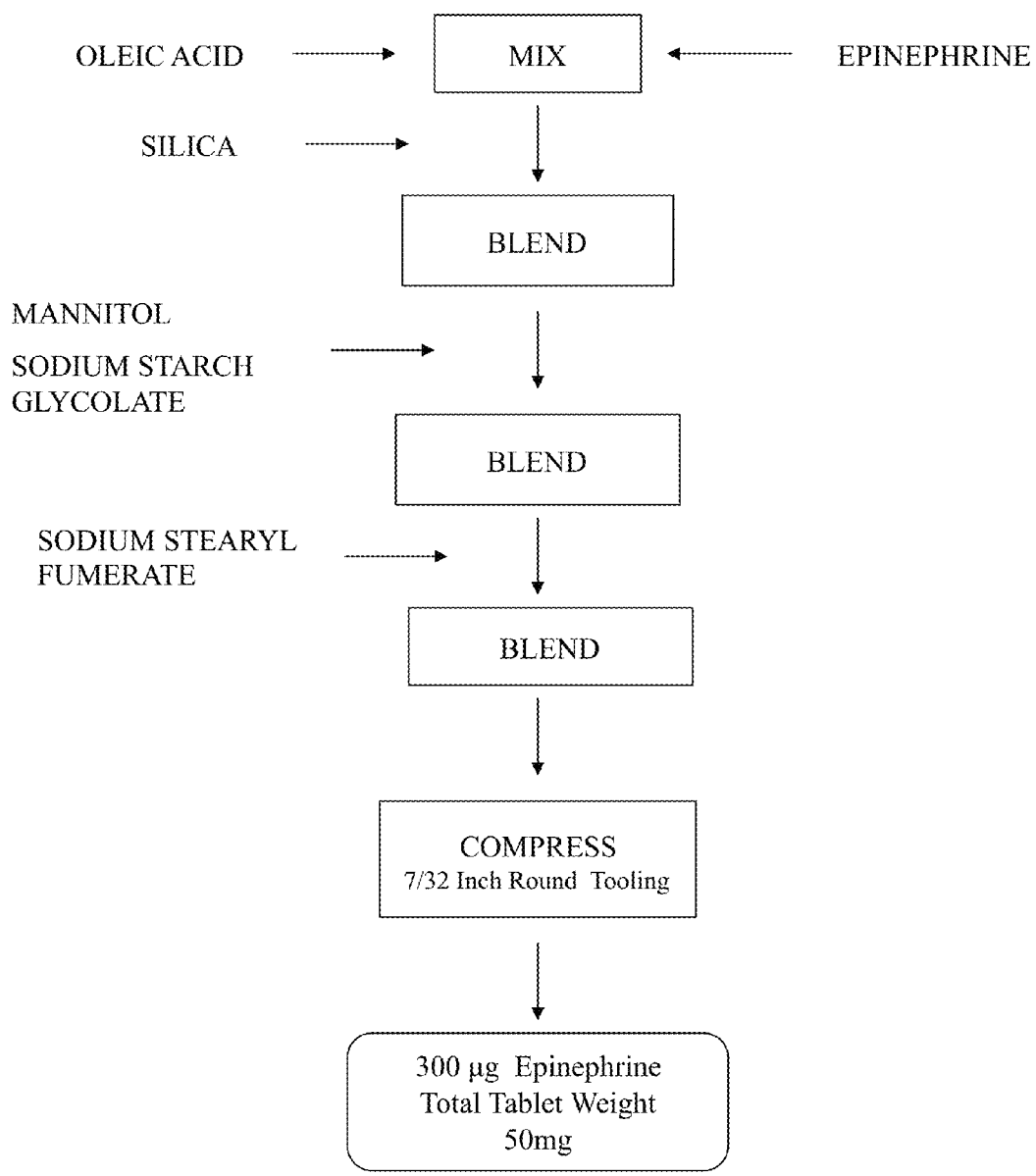
FIG. 3 is a schematic showing a method of manufacture of an epinephrine sublingual/buccal tablet according to the invention.

Method of manufacture. A method of manufacture for such sublingual/buccal tablet embodiments may be any suitable method known in the art including, but not limited to, the addition of the epinephrine LA or LA-solvate to premanufactured tablets, cold compressions with inert fillers and binders, direct tablet compression blends, direct powder blends, wet or dry granulations, molding, lyophilization, microencapsulation, freeze drying, spray-congealing, spray-drying, co-melt, spheronization, triturates, troching, powder layering, pelleting, encapsulation. An exemplary method of manufacture is outlined below and is schematically diagramed in FIG. 3.

STEP 1: Mix epinephrine, oleic acid and any other solvents together to form a solution.

STEP 2: Blend the epinephrine LA or LA-solvate with silica until homogeneous to form a silica carrier blend.

STEP 3: Add the silica carrier blend to mannitol and sodium starch glycolate and mix until homogeneous to form a further blend.

STEP 4: Add sodium stearyl fumarate to the further blend and blend until well lubricated to form a lubricated blend.

STEP 5: Compressing the lubricated blend into tablets using 7/32" round tooling.

Method of packaging. The sublingual/buccal tablets may be packaged in such a manner as to aid in maintaining epinephrine stability. Packaging methods and materials may include, but are not limited to, blister packaging in a foil/foil, foil/Acrylonitrile, foil/Polychlorotrifluoroethylene laminates.

Method of Use: In an embodiment, a buccal/sublingual tablet formulation according to the invention is useful in the treatment of severe allergic reactions to insect bites or stings, foods, drugs, and other allergens, as well as idiopathic and exercise induced anaphylaxis. This therapy is designed to allow allergic patient to abort a hyper immune response such as anaphylaxis. The typical treatment regiment starts by placing a 300 µg epinephrine sublingual tablet under the tongue and leaving it undistributed until dissolved, typically within 5 minutes, whenever there is an allergic reaction. This can be supplemented with additional sublingual tablets until the allergic response is ameliorated. The dosage range for this embodiment may vary from 200 µg to 1000 µg.

Example III

Fentanyl

Fentanyl transmucosal delivery is first line therapy for management of breakthrough cancer pain in patients with malignancies who are already tolerant to opioid therapy for their underlying persistent cancer pain. The embodiments as given herein have several advantages over the current therapy. First, the current transmucosal therapy uses a lollipop as the delivery system. The inherent implication and dangers of placing a potent opiate in the form of a candy attractive to children cannot be trivialized. Further, the current therapy takes over 20 minutes to reach maximum plasma concentrations. Thus pain relief is delayed far longer than would be desired. Hence the invention provides, in an embodiment, a fentanyl sublingual/buccal tablet to rapidly dissolve under the tongue, providing fast onset of action and pain relief for a cancer patient. Further, it is much safer for the family environment than a lollipop, which requires the disposal of potent, opioid-laden delivery systems.

In one embodiment, the invention provides a 200 μg strength fentanyl sublingual/buccal tablet having a total weight around 50 mg and nominal dimensions of about 0.55 cm in diameter and a thickness of about 0.15 cm. In one embodiment, the ionic pharmaceutical agent is fentanyl and the lipophilic species with which it is combined is oleic acid. The molar ratio of the lipophilic species to ionic pharmaceutical agent in this embodiment is not less than about 1:1. However, a molar excess of the lipophilic species, in this example oleic acid, may be used, e.g. 1.2:1. Embodiments are described herein. In certain embodiments, the LA may require the use of a solvent to stabilize or solubilize the LA, e.g. ethyl oleate and polyethylene glycol 400. In certain embodiments, the liquid LA or LA-solvate requires the use of an adsorbent/absorbent in order to convert it into a flowable powder suitable for use in direct compression tableting. An exemplary adsorbent is a silica Other excipients may be used in order to manufacture a rapidly disintegrating, directly compressible tablet. An exemplary diluent is the water-soluble, direct compression tableting excipient mannitol. In order to rapidly break the tablet apart upon administration, a disintegrant is used. An exemplary disintegrant is sodium starch glycolate. An exemplary tablet lubricant is sodium stearyl fumarate. Exemplary embodiments are provided in Table III.

TABLE III

200 μg Fentanyl Sublingual/Buccal Tablet Formulations

| | AMOUNT (mg/tablet) Embodiment 1 | AMOUNT (mg/tablet) Embodiment 2 | AMOUNT (mg/tablet) Embodiment 3 |
|---|---|---|---|
| Fentanyl | 0.20 | 0.20 | 0.20 |
| Oleic Acid | 0.17 | 0.17 | 0.17 |
| Ethyl oleate | — | 5.13 | — |
| Polyethylene glycol 400 | — | — | 5.13 |
| Silica | 0.27 | 4.00 | 4.00 |
| Mannitol | 47.36 | 38.50 | 38.50 |
| Sodium Starch Glycolate | 1.50 | 1.50 | 1.50 |
| Sodium Stearyl Fumarate | 0.50 | 0.50 | 0.50 |
| Total Tablet Weight | 50.00 | 50.00 | 50.00 |

Figure 4:
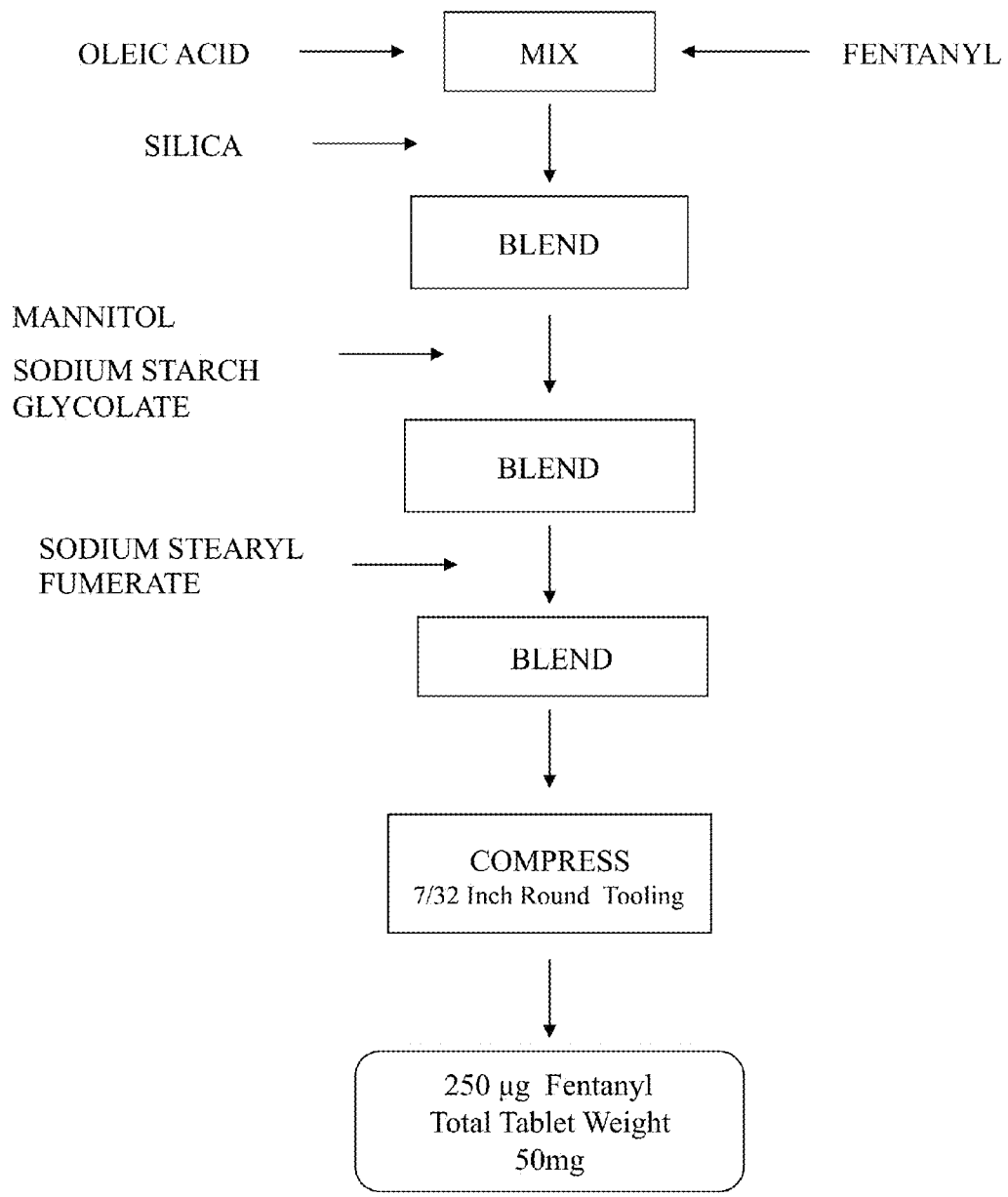
FIG. 4 is a schematic showing a method of manufacture of a fentanyl sublingual/buccal tablet according to the invention.

Method of manufacture: A method of manufacture for such sublingual/buccal tablet embodiments may be any suitable method known in the art including, but not limited to, the addition of the fentanyl LA or LA-solvate to pre-manufactured tablets, cold compressions with inert fillers and binders, direct tablet compression blends, direct powder blends, wet or dry granulations, molding, lyophilization, microencapsulation, freeze drying, spray-congealing, spray-drying, co-melt, spheronization, triturates, troching, powder layering, pelleting, encapsulation. An exemplary method of manufacture is outlined below and is schematically represented in FIG. 4.

STEP 1: Mix fentanyl, oleic acid and any other solvents together to form a solution.

STEP 2: Blend the fentanyl LA or LA-solvate with silica until homogeneous to form a silica carrier blend.

STEP 3: Add the silica carrier blend to mannitol and sodium starch glycolate and mix until homogeneous to form a further blend.

STEP 4: Add sodium stearyl fumarate to the further blend and blend until well lubricated to form a lubricated blend.

STEP 5: Compressing the lubricated blend into tablets using 7/32" round tooling.

Method of packaging. The sublingual/buccal tablets may be packaged in such a manner as to aid in maintaining fentanyl stability. Exemplary packaging methods and materials include, but not limited to, blister packaging in a foil/foil, foil/Acrylonitrile, foil/Polychlorotrifluoroethylene laminates.

Method of Use: In an embodiment, a buccal/sublingual tablet formulation according to the invention is useful in the treatment of severe breakthrough cancer pain in patients with malignancies who are already tolerant to opioid therapy for their underlying persistent cancer pain. This therapy is designed to allow the cancer patient to self-administer the treatment. The treatment regiment starts by placing a 200 μg fentanyl sublingual tablet under the tongue and leaving it undistributed until dissolved, typically within 5 minutes, whenever there is an occurrence of breakthrough pain. Depending on the level of opiate tolerance in each patient, other dosage strengths may be used in treatment of each individual patient. The range of dosage strength can be from 50 μg to 5000 μg.

Example IV

Alendronic Acid

Bisphosphonates are potent inhibitors of bone resorption and are used in osteoporosis and Paget's disease of the bone. These are also used in the treatment of bone metastases and hypercalcaemia of malignancies. The most commonly used bisphosphonates are alendronic acid, clodronic acid and etidronic acid. The embodiments as given herein have several advantages over the current bisphosphonate therapies. First, the current therapy is a tablet given by mouth or by IV injection. Oral administration is associated with a number of severe side effects including oesophagitis, esophageal erosions and ulcerations, dyspepsia, diarrhea, abdominal pain, and peptic ulcers. Further, oral bioavailability is very poor, in the range of 0.4 to 0.7% for alendronic acid and from to 1 to 6% for clodronic and etidronic acids. When administrated with food, bioavailability can be significantly reduced even to the level of being negligible. For alendronic acid, the usual daily dosage is 5 to 10 mg for osteoporosis and the dosage for Paget's disease is about 40 mg per day. The present invention provides, in one embodiment, a sublingual/buccal tablet that is designed to rapidly dissolve under the tongue. This avoids the potentially serious side effects and the poor and erratic bioavailability observed from oral delivery.

In one embodiment, a 100 μg strength alendronic sublingual/buccal tablet has a total weight of about 50 mg, and nominal dimensions of about 0.55 cm in diameter and a thickness of about 0.15 cm. The ionic pharmaceutical agent in this example is alendronic acid combined with the lipophilic species oleic acid. Alendronic acid has an amine functional group in additional to acid functional groups in addition to acid functional groups. The molar ratio between these two species in this example is at least about 1:1. However, since alendronic acid contains two phosphoric acid groups, a lipophilic amine or amide, in this example hexetidine, may need. The molar ratio is at least about 1:1 but may be increased to about 2:1. In certain embodiments, the LA may require the use of a solvent to stabilize or solubilize the LA, e.g., ethyl oleate and polyethylene glycol 400. Embodiments are described herein. The LA or LA-solvate may require the use of an adsorbent/absorbent in order to convert it into a flowable powder suitable for use in direct compression tableting. In one embodiment, the adsorbent is a silica. In order to manufacture a rapidly disintegrating, directly compressible tablet other excipients may be needed. In one embodiment, the diluent is the water-soluble, direct compression tableting excipient mannitol. In order to rapidly break the tablet apart upon administration, a disintegrant is used. In one embodiment, the disintegrant is sodium starch glycolate. In one embodiment, the tablet lubricant is sodium stearyl fumarate. Several embodiments are given in Table IV.

TABLE IV

100 μg Alendronic Acid Sublingual/Buccal Tablet Formulations

| INGREDIENT | AMOUNT (mg/tablet) Embodiment 1 | AMOUNT (mg/tablet) Embodiment 2 | AMOUNT (mg/tablet) Embodiment 3 | AMOUNT (mg/tablet) Embodiment 4 |
|---|---|---|---|---|
| Alendronic acid | 0.10 | 0.10 | 0.10 | 0.10 |
| Oleic acid | 0.12 | 0.13 | 0.13 | 0.13 |
| Hexetidine | — | 0.27 | 0.27 | 0.27 |
| Ethyl oleate | — | — | 5.00 | — |
| Polyethylene glycol 400 | — | — | — | 5.00 |
| Silica | 0.13 | 0.35 | 4.00 | 4.00 |
| Mannitol | 47.65 | 47.16 | 38.51 | 38.51 |
| Sodium Starch Glycolate | 1.50 | 1.50 | 1.50 | 1.50 |
| Sodium Stearyl Fumarate | 0.50 | 0.50 | 0.50 | 0.50 |
| Total Tablet Weight | 50.00 | 50.00 | 50.00 | 50.00 |

Method of Manufacture

Figure 5:
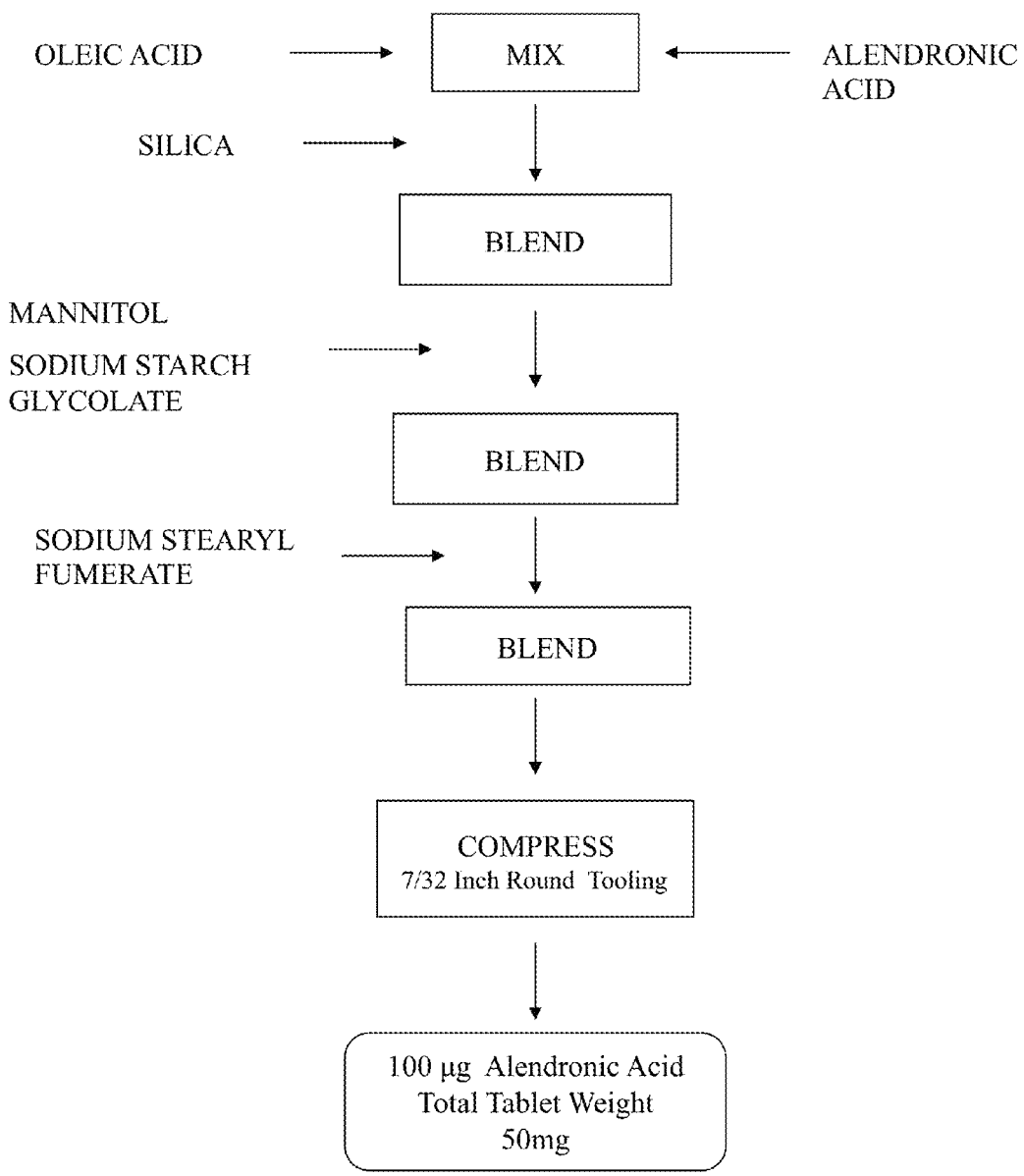
FIG. 5 is a schematic showing a method of manufacture of alendronic acid sublingual/buccal tablet according to the invention.

The method of manufacture for this sublingual/buccal tablet embodiment may be any suitable method know in the art including, but not limited to, the addition of the alendronic acid LA or LA-solvate to premanufactured tablets, cold compressions with inert fillers and binders, direct tablet compression blends, direct powder blends, wet or dry granulations, molding, co-melt, lyophilization, microencapsulation, freeze drying, spray-congealing, spray-drying, spheronization, triturates, troching, powder layering, pelleting, encapsulation. One exemplary method of manufacture is outlined below and is schematically in FIG. 5.

STEP 1: Mix alendronic acid, oleic acid, and any other the lipophilic species or solvents together to form a solution.

STEP 2: Blend the alendronic acid LA or LA-solvate with silica until homogeneous to form a silica carrier blend.

STEP 3: Add the silica carrier blend to mannitol and sodium starch glycolate and mix until homogeneous to form a further blend.

STEP 4: Add sodium stearyl fumarate to the further blend and blend until well lubricated to form a lubricated blend.

STEP 5: Compressing the lubricated blend into tablets using 7/32" round tooling.

Method of Packaging: The sublingual/buccal tablets may be packaged in such a manner as to aid in maintaining stability. Exemplary packaging methods and materials include blister packaging in a foil/foil, foil/Acrylonitrile, foil/Polychlorotrifluoroethylene laminates.

Method of Use: In an embodiment, a buccal/sublingual tablet formulation according to the invention is useful in the treatment of osteoporosis and Paget's disease of the bone. It can also be used in the treatment of bone metastases and hypercalcaemia of malignancies. In one embodiment the treatment regiment starts by placing a 100 μg alendronic acid sublingual tablet under the tongue and leaving it undistributed until dissolved, typically within 5 minutes. The treatment is given once a day. The dosage range for this embodiment may be from 50 μg to 1000 μg.

Example V

Clorazepic Acid

Clorazepic acid is a benzodiazepine used mainly for the treatment of anxiety, adjunct therapy for epilepsy and alcohol withdrawal syndrome. It is administered orally, intravenously and intramuscularly. Orally it is typically given in divided doses. The embodiments as given herein have several advantages over the current therapies. A patient undergoing alcohol withdrawal will typically exhibit signs of nausea and vomiting. Any orally administered therapy during times of alcohol withdrawal runs the risk of being not efficacious as vomiting can eliminate the dosage. Further, for children, geriatric and depilated patients, swallowing a tablet can be difficult. Since clorazepic acid is used in the relief of anxiety for elderly and debilitated patients and also as an adjunct therapy for epilepsy in children, having a convenient dosage form that does not require swallowing a tablet for administration provides a better therapy. Another therapy for which benzodiazepines have been used is for panic attacks. Sublingual clorazepic may be useful in the treatment of panic attacks, particularly due to its rapid onset of action. Panic attacks and agoraphobia could be avoided by administered the sublingual tablet just prior to the patient encountering a situation known to induce such attacks. Further, it could be used at the first signs of an attack, due to its rapid absorption, and thereby abort the attack.

Exemplary Embodiment

In one embodiment, a 5.75 mg strength clorazepic acid sublingual/buccal tablet has a total weight around 100 mg, and nominal dimensions of about 0.64 cm in diameter and a thickness of about 0.20 cm. The ionic pharmaceutical agent is clorazepic acid combined with the lipophilic species hexetidine. The molar ratio between these two species being not less than about 1:1. This LA may also require the use of a solvent. The LA or LA-solvate may require the use of an adsorbent/absorbent in order to convert it into a flowable powder suitable for use in direct compression tableting. One exemplary adsorbent for this embodiment is a silica. In order to manufacture a rapidly disintegrating, directly compressible tablet, other excipients may be needed. In one embodiment the diluent is the water-soluble, direct compression tableting excipient mannitol. In order to rapidly break the tablet apart upon administration a disintegrant is used. In one embodiment, the disintegrant is sodium starch glycolate. In one embodiment, the tablet lubricant is sodium stearyl fumarate. Several embodiments, are given in Table V below.

TABLE V

5.75 mg Clorazepic Acid Sublingual/Buccal Tablet Formulations

| INGREDIENT | AMOUNT (mg/tablet) Embodiment 1 | AMOUNT (mg/tablet) Embodiment 2 | AMOUNT (mg/tablet) Embodiment 3 |
|---|---|---|---|
| Clorazepic acid | 5.75 | 5.75 | 5.75 |
| Hexetidine | 6.25 | 6.25 | 6.25 |
| Ethyl oleate | — | 2.00 | — |
| Polyethylene glycol 400 | — | — | 2.00 |
| Silica | 8.00 | 9.00 | 9.00 |
| Mannitol | 76.00 | 73.00 | 73.00 |
| Sodium Starch Glycolate | 3.00 | 3.00 | 3.00 |
| Sodium Stearyl Fumarate | 1.00 | 1.00 | 1.00 |
| Total Tablet Weight | 100.00 | 100.00 | 100.00 |

Figure 6:
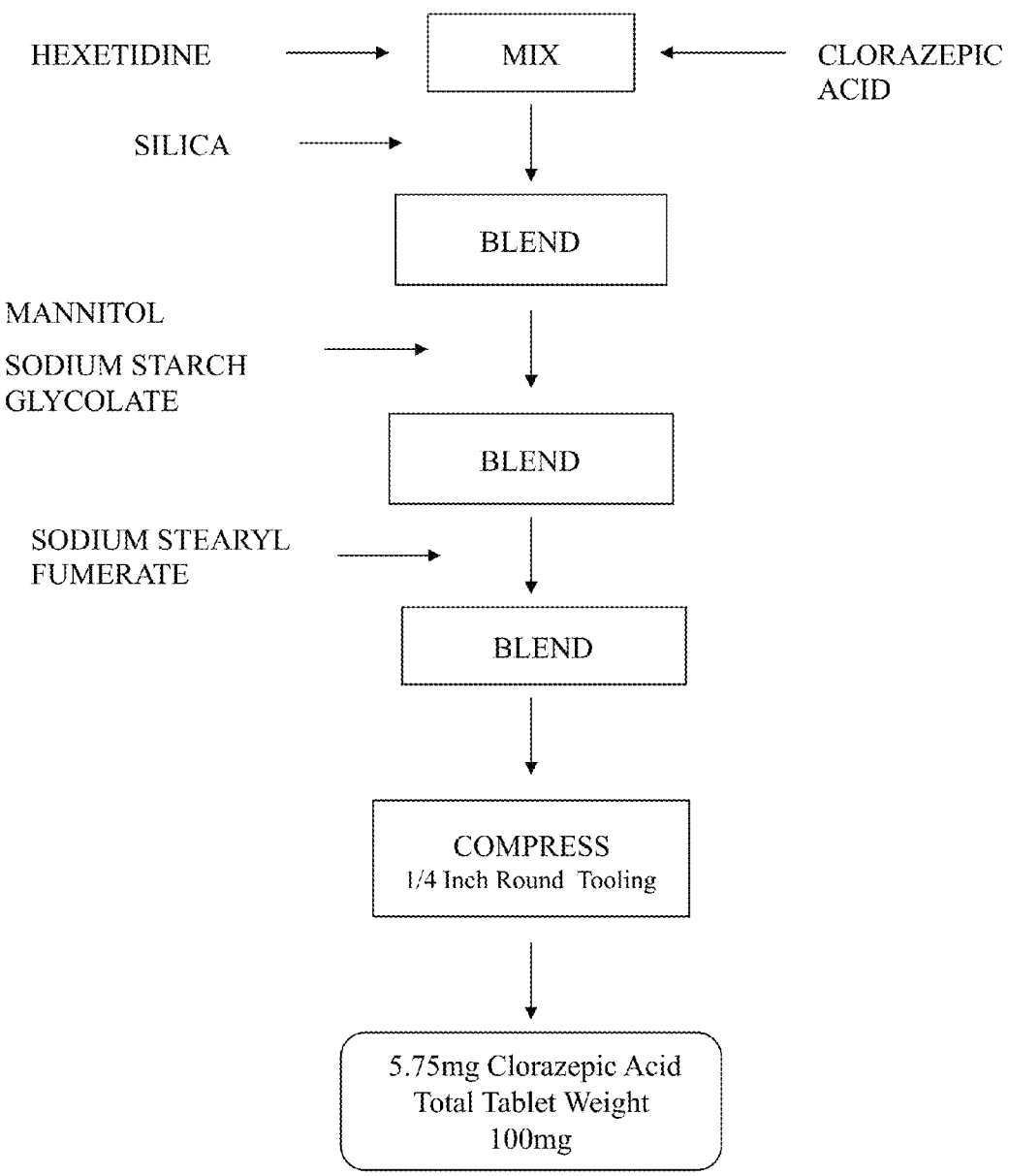
FIG. 6 is a schematic showing a method of manufacture of a clorazepic acid sublingual/buccal tablet according to the invention.

Method of Manufacture: The method of manufacture for this sublingual/buccal tablet embodiment may be any suitable method know in the art including, but not limited to, the addition of the clorazepic acid LA or LA-solvate premanufactured tablets, cold compressions with inert fillers and binders, direct tablet compression blends, direct powder blends, wet or dry granulations, molding, spray-congealing, lyophilization, freeze-drying, microencapsulation, co-melt, spray-drying, spheronization, triturates, troching, powder layering, pelleting, encapsulation. One method of manufacture is outlined below and is schematically represented in FIG. 6.

STEP 1: Mix clorazepic acid, hexetidine and any other solvents together until a solution is prepared.

STEP 2: Blend the clorazepic acid LA or LA-solvate with silica until homogeneous.

STEP 3: Add the clorazepic LA or LA-solvate silica carrier blend to mannitol and sodium starch glycolate and mix until homogeneous.

STEP 4: Add sodium stearyl fumarate to the blend from Step 3 and blend until well lubricated.

STEP 5: The lubricated blend from Step 4 is compressed into tablets using ¼" round tooling.

Method of Packaging: The sublingual/buccal tablets may be packaged in such a manner as to aid in maintaining stability. Exemplary packaging methods and materials include, but are not limited to, blister packaging in a foil/foil, foil/Acrylonitrile, foil/Polychlorotrifluoroethylene laminates.

Method of Use: In an embodiment, a sublingual/buccal tablet formulation according to the invention is useful in the treatment of alcohol withdrawal, anxiety or epilepsy. This therapy is designed to allow the patient to administer the therapy without having to swallow the dosage form. The typical treatment regiment starts by placing a 5.75 mg clorazepic acid sublingual tablet under the tongue and leaving it undistributed until dissolved, typically within 5 minutes. This can be supplemented with additional sublingual tablets during the day, typically three times per day; however, under certain treatment regimens one tablet at night may be given. For panic attacks and agoraphobia, the patient can administer the sublingual tablet just prior to encountering a panic-inducing situation or at the onset of an attack. The dosage range for this embodiment can be from 2 mg to 12 mg of clorazepic acid.

In one embodiment, the pharmaceutical composition of the subject invention is provided as an oral dosage form for buccal or sublingual administration, e.g. films, lozenges, pills and tablets. In the following illustrative embodiments, the oral dosage form is provided as a tablet. In the following illustrative embodiments, the treatment is directed to subjects in need of hormone replacement with estradiol or other indications for which estradiol can be used as a therapeutic and wherein increasing the oral absorption and bioavailability, while shortening the onset of estradiol action is provided.

It is understood by the skilled artisan, that use of the term "about" includes the range as stated, are within what is normally acceptable in the pharmaceutical industry. The US Pharmacopeia allows a plus and minus range of 10% in the assay for the active ingredient in most solid dosage forms. The Food and Drug Administration (FDA) has a published Guidances for changes in levels of common excipient classes that are considered unlikely to have any detectable impact on formulation quality and performance (Guidance for Industry: Immediate Release Solid Oral Dosage Forms Scale-Up and Post approval Changes: Chemistry, Manufacturing, and Controls, In Vitro Dissolution Testing, and In Vivo Bioequivalence Documentation). Under this Guidance the water-soluble solid excipient has an allowable change is ±5%, for a disintegrant it is ±1%, for a lubricant it is ±1%. Although the Guidance is not specific for the complimentary lipophilic species, co-solvent or adsorbent and considering the range for the active is ±10%, the value for these excipients should be no different than the active as their use in the formulation is directly dependent on the active's level.

As illustrated, tablets are used for the treatment and such tablets contain from about 0.05 mg to about 2 mg of estradiol, from about 1 mg to about 50 mg of a liquid polyethylene glycol (PEG), illustrated by, albeit not limited to, PEG 400, from about 0.1 mg to about 50 mg of a solid adsorbent, when included in a particular formulation, illustrated by, albeit not limited to silica, and from about 25 mg to about 500 mg of a water-soluble solid excipient, illustrated by, albeit not limited to, spray dried mannitol. In some instances the water-soluble solid excipient, illustrated by, albeit not limited to, spray dried mannitol, may function as the only solid adsorbent and as the water-soluble solid excipient in the particular formulation. In the case of certain formulations, an effective amount of a co-solvent may be necessary in order to enhance the transport of the active ingredient through the mucosal membrane. In such instances up to 25 mg per tablet is considered an effective amount to facilitate such transport, illustrated by, albeit not limited to, ethanol.

The steps of dissolving the active ingredient, e.g. estradiol, to form an active ingredient-containing solution followed by contacting of the active ingredient-containing solution with the solid absorbent/adsorbent carrier whereby said active ingredient-containing solution is coated, absorbed or adsorbed onto said carrier are unique to the instant invention, and the carrying out of said steps are what allow for the formation of a unique solid dosage form which enables increased oral absorption and bioavailability while shortening onset of active ingredient action upon administration of the novel solid dosage form via the buccal or sublingual route.

In the illustrated embodiments, the tablet further contains at least one disintegrant and one lubricant. Although the disintegrant has been exemplified in the formulations in Tables 6, 7 and 8 as sodium starch glycolate, it is nevertheless within the purview of this invention to substitute any functionally equivalent disintegrant, illustrated by, but not limited to, crospovidone, croscarmellose sodium, low-substituted hydroxypropyl cellulose, starch, microcrystalline cellulose and mixtures thereof. The content of the disintegrant is from about 0.5 mg to about 50 mg.

In the illustrated embodiments, the tablet further contains at least one lubricant. Although the lubricant has been exemplified in the formulations in Tables 6, 7 and 8 as sodium stearyl fumarate, it is nevertheless within the purview of this invention to substitute any functionally equivalent lubricant, illustrated by, but not limited to, magnesium stearate, stearic acid, sodium lauryl sulfate, talc, polyethylene glycol, calcium stearate and mixtures thereof. The content of the lubricant is from about 0.1 mg to about 15 mg.

Example VI

In one embodiment, the invention provides a 0.5 mg strength estradiol sublingual tablet having a total tablet weight of about 100 mg, wherein the tablet comprises the drug, a solid adsorbent, such as silica; a water-soluble solid excipient, such as mannitol; a disintegrant, such as sodium starch glycolate; and a lubricant, such as sodium stearyl fumarate. In such an embodiment, estradiol is mixed with PEG 400. An exemplary formulation in accordance with the described formulation of this embodiment is provided in Table VI, below.

TABLE VI 0.5 mg Estradiol Sublingual Tablet Formulation

| INGREDIENT | AMOUNT (mg/tablet) |
|---|---|
| Estradiol | 0.5 |
| PEG 400 | 10.0 |
| Silica | 6.5 |
| Mannitol | 78.0 |
| Sodium Starch Glycolate | 3.0 |
| Sodium Stearyl Fumarate | 2.0 |
| Total Tablet Weight | 100.0 |

Example VII

In one embodiment, the invention provides a 1 mg strength estradiol sublingual tablet having a total tablet weight of about 250 mg. In this exemplary embodiment, estradiol is mixed with PEG 400 and the co-solvent ethanol. An exemplary formulation manufactured for this embodiment in accordance with the subject invention is provided in Table VII, below.

TABLE VII 1 mg Estradiol Sublingual Tablet Formulation

| INGREDIENT | AMOUNT (mg/tablet) |
|---|---|
| Estradiol | 1.0 |
| PEG 400 | 20.0 |
| Ethanol | 4.0 |
| Silica | 15.0 |
| Mannitol | 200.0 |
| Sodium Starch Glycolate | 6.0 |
| Sodium Stearyl Fumarate | 4.0 |
| Total Tablet Weight | 250.0 |

Example VIII

In one embodiment, the invention provides a 0.1 mg strength estradiol sublingual tablet having a total tablet weight of about 160 mg. In this exemplary embodiment, estradiol is mixed with PEG 400 and added to spray dried mannitol, which functions as the water-soluble solid excipient and solid adsorbent. An exemplary formulation manufactured for this embodiment in accordance with the subject invention is provided in Table VIII, below.

TABLE VIII 0.1 mg Estradiol Sublingual Tablet Formulation

| INGREDIENT | AMOUNT (mg/tablet) |
|---|---|
| Estradiol | 0.1 |
| PEG 400 | 2.0 |
| Mannitol | 150.4 |
| Sodium Starch Glycolate | 4.5 |
| Sodium Stearyl Fumarate | 3.0 |
| Total Tablet Weight | 160.0 |

Example IX

Figure 7:
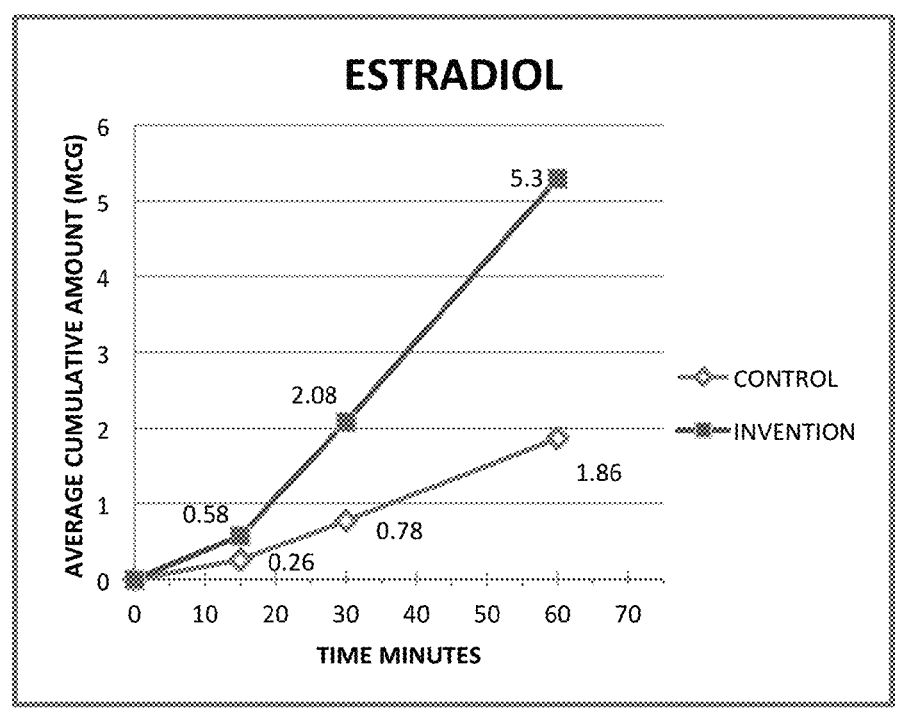
FIG. 7 is a graph from an oral mucosa tissue permeation study comparing 0.5 mg estradiol tablet formulated as per Example 6 of the invention.

FIG. 7 is a graph from an oral mucosa tissue permeation study comparing 0.5 mg estradiol tablet formulated as per Example 6 of the invention using polyethylene glycol 400 as the solvent and a control 0.5 mg estradiol tablet wherein the estradiol is formulated in its solid state. This study was conducted using Epioral™ buccal tissue mounted in a Franz cell and the drug concentration measured by high pressure liquid chromatograph (HLPC) in the receiver solution over time. The tablets were wetted with 1.5 ml phosphate buffered saline (PBS) at a pH of 7.2, which was added to the donor side at the beginning of the test, and samples were taken from the receiver side of the Franz cell at the time points depicted in the graph below. The receiver solution is 1% Tween 20 in PBS, so as to increase the solubility of the estradiol in the receiver solution. This data shows that the permeation of estradiol from the tablet formulated as per the invention is about 3 times faster than the control, see calculation below. This faster permeation rate through the buccal tissue shows that invention has increased absorption rate and bioavailability and faster onset than the control.

Permeation rate between time points 30 and 60 minutes is calculated as the slope of each line:

INVENTION=5.3 mcg–0.58 mcg/45 minutes=0.105 mcg/minute

CONTROL=1.86 mcg–0.26 mcg/45 minutes=0.036 mcg/minute

Ratio of INVENTION to CONTROL=0.107/0.036=2.92

Example X

A method of manufacture for a tablet according to an embodiment of the subject invention for sublingual/buccal administration may employ any suitable method known in the art including, but not limited to, the addition of the estradiol and PEG 400 mixture with or without a co-solvent to pre-manufactured tablets, cold compressions with inert fillers and binders, direct tablet compression blends, direct powder blends, wet or dry granulations, molding, lyophilization, microencapsulation, freeze drying, spray-congealing, spray-drying, co-melt, spheronization, triturates, troching, powder layering, pelleting, encapsulation.

Figure 8:
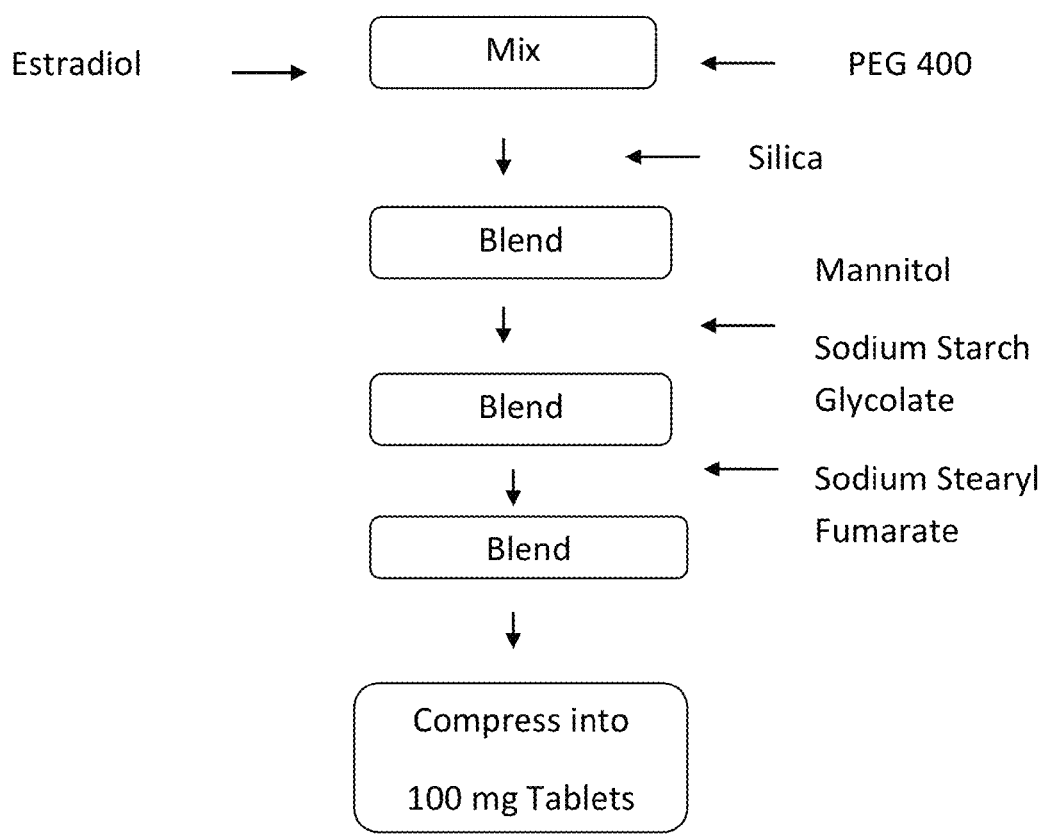
FIG. 8 is a schematic showing a method of manufacture of an estradiol sublingual/buccal tablet according to the invention.

An exemplary method for the manufacture of a direct compression tablet of the formulation given in Example 6 is outlined below and is schematically diagramed in FIG. 8:

Exemplary Embodiment

STEP 1: Mix estradiol and PEG 400 together.

STEP 2: Blend the estradiol and PEG 400 mixture from Step 1 with silica until homogeneous to form a silica blend.

STEP 3: Add to the silica blend from Step 2, mannitol and sodium starch glycolate and mix until homogeneous to form a further blend.

STEP 4: Add sodium stearyl fumarate to the further blend from Step 3 and blend until well lubricated to form a lubricated blend.

STEP 5: Compressing the lubricated blend from Step 4 into 100 mg tablets using ¼ inch round tooling.

Method of packaging. The sublingual/buccal tablets may be packaged in such a manner as to aid in maintaining stability. Packaging methods and materials may include, but are not limited to, blister packaging in a foil/foil, foil/Acrylonitrile, foil/Polychlorotrifluoroethylene laminates for blister packaging or glass and plastic bottles.

Method of Use: In an embodiment, estradiol sublingual tablet formulation according to the invention is useful in the treatment of low estrogen levels and other disease states for which estradiol is an effective therapeutic. The typical treatment regimen starts by placing the estradiol tablet under the tongue and leaving it undisturbed for about 5 to 15 minutes.

All references cited herein are incorporated herein by reference. Where the meaning of any term as used within the application itself differs from the meaning of that same term in any of the references, the meaning of the term as used within the application itself controls.

It is to be understood that the embodiments described above are intended to be illustrative and not restrictive. Many other embodiments will be apparent to those of skill in the art once they have read the above description. The foregoing description and embodiments are therefore merely exemplary and are not intended to limit the scope of the invention, which encompasses all equivalents of what is described herein and set forth particularly by the appended claims.

REFERENCES

M. Trotta, E. Urazio, E. Peira and C. Pulitano, "Influence of ion pairing on topical delivery of retinoic acid from microemulsions", J. Control Release, 2003, Vol. 86, pp 315-321.

Beckett and Hossie: Buccal Absorption of Drugs, in Handbook of Experimental Pharmacology, ed. B. B. Brodie and J. R. Gillette; Springer-Verlag, Berlin (1971). Ch. 3.

H. R. Leipold and E. Quadros: Nicotine Permeation Through Buccal Cultures. in Proceed. Intern. Symp. Control. Rel. Bioact. Mater., Controlled Release Society, 20 (1993), 242-243

R. M. Diamond, "Aqueous solution behavior of large univalent ions. A new type of ion-pairing", J. Physic. Chem. Vol. 39 (1967), pp 2513-2517.

Pomerleau Ann. Behav. Med. 1998, Vol. 36, pp 158-163.

D. Quintanar-Guerrero, E. Allemann, H. Fessi and E. Doelker, "Applications of the ion-pair Concept to Hydrophilic Substances with Special Emphasis on Peptides", Pharm. Res., 1997, Vol. 14, No. 2, pp 119-127.

G. L. Amidon, H. Lennemas, V. P. Shah, J. R Crison, "A Theoretical Basis for a Biopharmaceutical Drug Classification: The Correlation of in Vitro Drug Product Dissolution and in Vivo Bioavailability", Pharm. Res. 1995, Vol. 12, No. 3, pp 413420.

T. Hatanaka, T. Kamon, S. Morigaki, K. Katayama, T. Koizumi, "Ion Pair Skin Transport of a Zwitterionic Drug, Cephalexin", J. Control Res. 2000, Vol. 66, pp 63-71.

C. Valenta, U. Siman, M. Kratzel, J. Hadgraft, "The Dermal Delivery of Lignocaine: Influence of Ion Pairing", Inter. J. of Pharm. 2000, Vol. 197, pp 77-85.

S. Megwa, S. Cross, M. Whitehouse, H. Benson, M. Roberts, "Effect of Ion Pairing with Alkylamines on the In-vitro Dermal Penetration and Local Tissue Disposition of Salicylates", J. Pharm. Pharmacol. 2000, Vol. 52, No. 8, pp 929-940.

R. Neubert, "Ion Pair Transport Across Membranes", Pharm. Res. 1989, Vol. 6, No. 9, pp 743-747.

M. Gallarate, M. Gasco, M. Trotta, P. Chetoni, M. Saettone, "Preparation and Evaluation In vitro of solutions and O/W microemulsions Containing Levobunolol as Ion-Pair", Interm J. of Pharm. 1993, Vol. 100, pp 219-225.

Product Insert for COMMIT™ (nicotine polacrilex lozenge) GlaxoSmith Kline Consumer Healthcare, L. P.

Product Insert for ACTIQ' (oral transmucosal fentanyl citrate) Cephalon, Inc.

Product Insert for EPIPEN' (epinephrine auto-injector) Dey,

S. Senel, A Hincal, "Drug Permeation Enhancement via Buccal Route: Possibilities and Limitations", J. of Control Rel. 2001, Vol. 72, pp 133-144.

"Oral transmucosal drug dosage using solid solution", October 1999 U.S. Pat. No. 6,264,981

U.S. Pat. No. 5,662,920

U.S. Pat. No. 6,630,498 M. Gudipati et al October 2003

U.S. Pat. No. 6,264,981 Zhang et al. July 2001

U.S. Pat. No. 5,132,114

U.S. Pat. No. 5,354,560

U.S. Pat. No. 5,449,521

U.S. Pat. No. 5,711,961

WO 03/055486 A1 Lindell et al., July 2003.

U.S. Pat. No. 6,248,760 P. Wilhelmsen, June 2001

U.S. Pat. No. 5,373,022 M. Fawzi et al September 1992.

U.S. Pat. No. 4,816,247 N. Desia et al March 1989.

U.S. Pat. No. 5,374,645 T. Kurihara-Bergstrom et al., December 1994.

U.S. Pat. No. 6,479,540 P. Constantinides et al., November 2002.

U.S. Pat. No. 6,395,713 L. Beigelman, et al., May 2002.

A. Gennaro (Ed.), Remingtons: The Science and Practice of Pharmacy, 20.sup.th edition, 2000, Lippincott Williams & Wilkins, Baltimore, Md.

S. Sweetman (Ed.) Martindale the Complete Drug Reference, 33.sup.rd edition, 2002, Pharmaceutical Press, London.

L. Murray (Ed.), Physicians Desk Reference, 58.sup.th edition, 2004, Thomson, Montvale, N.J.

D. Nissen (Ed.), Mosby's Drug Consult, 2003, Elsevier Science, St. Louis, Mo.

What is claimed is:

1. A pharmaceutical composition containing epinephrine in a solid dosage form for buccal or sublingual delivery, comprising:
    epinephrine;
    a solvent into which epinephrine is solvated; and
    a solid adsorbent onto which the solvated epinephrine is adsorbed,
    wherein epinephrine is in solution in the solid dosage form of the pharmaceutical composition.

2. The pharmaceutical composition of claim 1, further comprising a solid water-soluble excipient, a disintegrant, a lubricant, or mixtures thereof.

3. A method for treating disease states for which epinephrine is an effective therapeutic, in a patient in need thereof, comprising: sublingually or buccally administering to the patient a therapeutically effective amount of the pharmaceutical composition of claim 1.

4. The method of claim 3, wherein the composition further comprises a solid water-soluble excipient, a disintegrant, a lubricant, or mixtures thereof.

5. A pharmaceutical composition containing fentanyl in a solid dosage form for buccal or sublingual delivery, comprising:
   fentanyl;
   a solvent into which fentanyl is solvated; and
   a solid adsorbent onto which the solvated fentanyl is adsorbed,
   wherein fentanyl is in solution in the solid dosage form of the pharmaceutical composition.

6. The composition of claim 5, further comprising a solid water-soluble excipient, a disintegrant, a lubricant, or mixtures thereof.

7. A method for treating disease states for which fentanyl is an effective therapeutic, in a patient in need thereof, comprising: sublingually or buccally administering to the patient a therapeutically effective amount of the pharmaceutical composition of claim 5.

8. The method of claim 7, wherein the composition further comprises a solid water-soluble excipient, a disintegrant, a lubricant, or mixtures thereof.

9. A pharmaceutical composition containing alendronic acid in a solid dosage form for buccal or sublingual delivery, comprising:
   alendronic acid;
   a solvent into which alendronic acid is solvated; and
   a solid adsorbent onto which the solvated alendronic acid is adsorbed,
   wherein alendronic acid is in solution in the solid dosage form of the pharmaceutical composition.

10. The composition of claim 9, further comprising a solid water-soluble excipient, a disintegrant, a lubricant, or mixtures thereof.

11. A method for treating disease states for which alendronic acid is an effective therapeutic, in a patient in need thereof, comprising: sublingually or buccally administering to the patient a therapeutically effective amount of the pharmaceutical composition of claim 9.

12. The method of claim 11, wherein the composition further comprises a solid water-soluble excipient, a disintegrant, a lubricant, or mixtures thereof.

13. A pharmaceutical composition containing clorazepic acid in a solid dosage form for buccal or sublingual delivery, comprising:
   clorazepic acid;
   a solvent into which clorazepic acid is solvated; and
   a solid adsorbent onto which the solvated clorazepic acid is adsorbed,
   wherein clorazepic acid is in solution in the solid dosage form of the pharmaceutical composition.

14. The composition of claim 13, further comprising a solid water-soluble excipient, a disintegrant, a lubricant, or mixtures thereof.

15. A method for treating disease states for which clorazepic acid is an effective therapeutic, in a patient in need thereof, comprising: sublingually or buccally administering to the patient a therapeutically effective amount of the pharmaceutical composition of claim 14.

16. The method of claim 15, wherein the composition further comprises a solid water-soluble excipient, a disintegrant, a lubricant, or mixtures thereof.

\* \* \* \* \*